(12) United States Patent
Andrus et al.

(10) Patent No.: US 7,348,164 B2
(45) Date of Patent: Mar. 25, 2008

(54) UNIVERSAL MULTI-VARIANT DETECTION SYSTEM

(75) Inventors: Linda Andrus, New York, NY (US); Carmen Nicola Nichols, Philadelphia, PA (US)

(73) Assignee: The New York Blood Center, Inc., New York, NY (US)

( * ) Notice: Subject to any disclaimer, the term of this patent is extended or adjusted under 35 U.S.C. 154(b) by 338 days.

(21) Appl. No.: 10/399,843

(22) PCT Filed: Apr. 17, 2002

(86) PCT No.: PCT/US02/12035

§ 371 (c)(1),
(2), (4) Date: Sep. 2, 2003

(87) PCT Pub. No.: WO02/083927

PCT Pub. Date: Oct. 24, 2002

(65) Prior Publication Data

US 2004/0053284 A1      Mar. 18, 2004

Related U.S. Application Data

(60) Provisional application No. 60/284,334, filed on Apr. 17, 2001.

(51) Int. Cl.
*C12P 19/34*    (2006.01)
*C12Q 1/64*    (2006.01)

(52) U.S. Cl. .......................... 435/91.2; 435/6
(58) Field of Classification Search .................... None
See application file for complete search history.

(56) References Cited

U.S. PATENT DOCUMENTS 5,925,517 A * 7/1999 Tyagi et al. ................ 435/6
6,007,983 A * 12/1999 Dunn et al. ................. 435/5
6,037,130 A * 3/2000 Tyagi et al. ................ 435/6
6,117,635 A   9/2000 Nazarenko et al.
6,150,097 A   11/2000 Tyagi et al.

FOREIGN PATENT DOCUMENTS

WO      WO 00/68436      11/2000
WO      WO 01/07652      2/2001

OTHER PUBLICATIONS

Stauffer et al., "Genus Level Identification of Mycobacterium from Clinical Specimens by Using an Easy-To-Handle Mycobacterium-specific PCR Assay," Journal of Clinical Microbiology, Mar. 1998, vol. 36, No. 3, pp. 614-617.*
S. K. Poddar, "Symmetric vs asymmetric PCR and molecular beacon probe in the detection of a target gene of adenovirus," *Molecular and Cellular Probes, Academic Press*, 14: 25-32 (2000).
Barlow et al., "Analysis and Genotyping of PCR Products of the Amplicor HIV-1 Kit", *Journal of Virological Methods*, 52:65-74 (1995).
Jurinke et al., "Application of Nested PCR and Mass Spectrometry for DNA-Based Virus Detection: HBV-DNA Detected in the Majority of Isolated Anit-HBc Positive Sera," *Genetic Analysis: Biomolecular Engineering*, 14: 97-102 (1998).
Bennet et al., "A Quantative PCR Method for the Assay of HIV-1 Provirus Load in Peripheral Blood Mononuclear Cells," *Journal of Virological Methods, Amsterdam*, 83: 11-20 (1999).
Tyagi et al., "Molecular Beacons: Probes that Fluoresce upon Hybridization," *Nature Biotechnology*, 14: 303-308 (Mar. 1996).
Tyagi et al., "Multicolor Molecular Beacons for Allele Discrimination," *Nature Biotechnology*, 16: 49-53 (Jan. 1998).
Abravaya et al., "Detection of Point Mutations with a Modified Ligase Chain Reaction (Gap-LCR)," *Nucleic Acids Research*, 23(4): 675-682 (1995).
Landegren et al., "A Ligase-Mediated Gene Detection Technique," *Science* 241: 1077-1080 (Aug. 26, 1988).

* cited by examiner

*Primary Examiner*—Young J. Kim
(74) *Attorney, Agent, or Firm*—Hoffmann & Baron, LLP

(57) ABSTRACT

The present invention provides a method to diagnostically detect the variants of a given pathogen, such as HIV, hepatitis C, hepatitis B (HBV), Parvovirus B19, etc., with the use of a single detection probe.

35 Claims, 14 Drawing Sheets

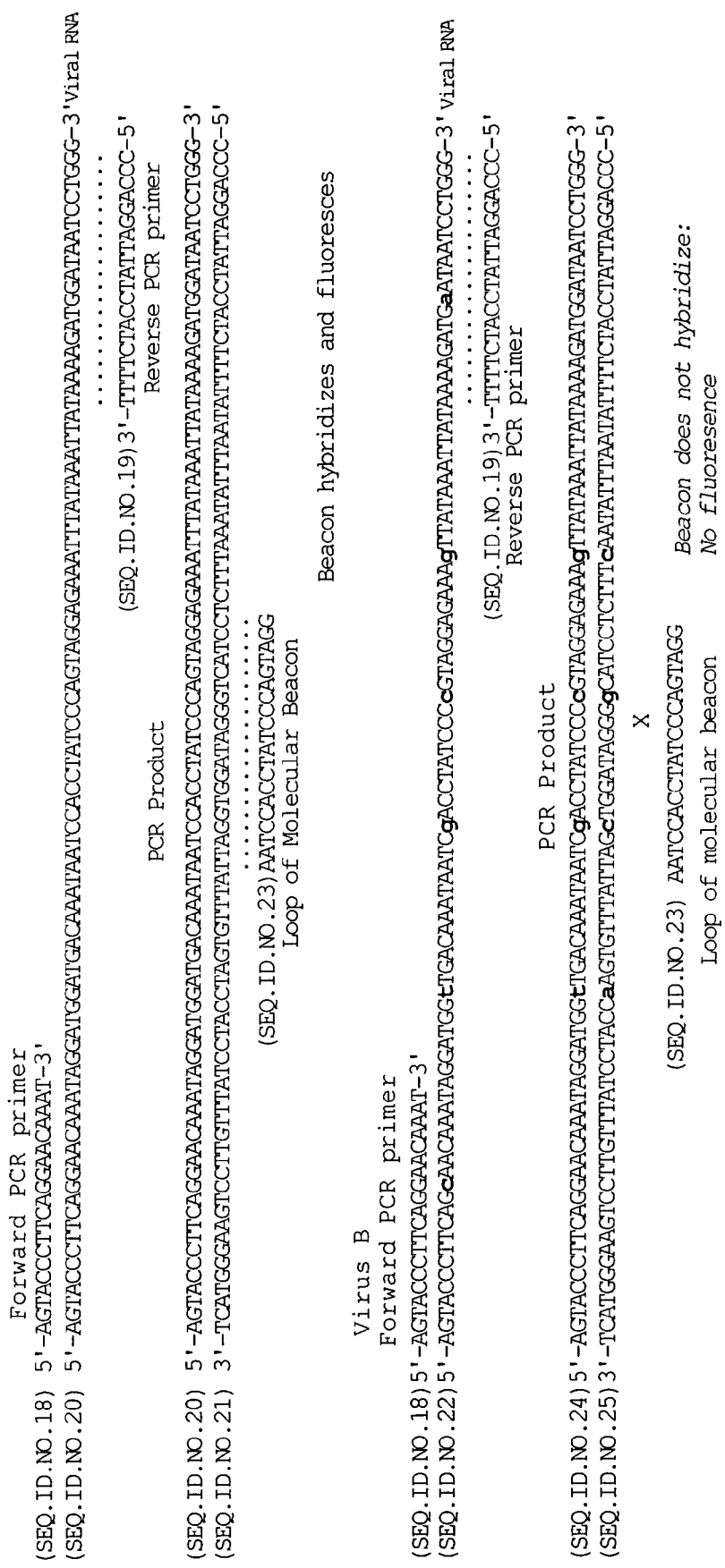

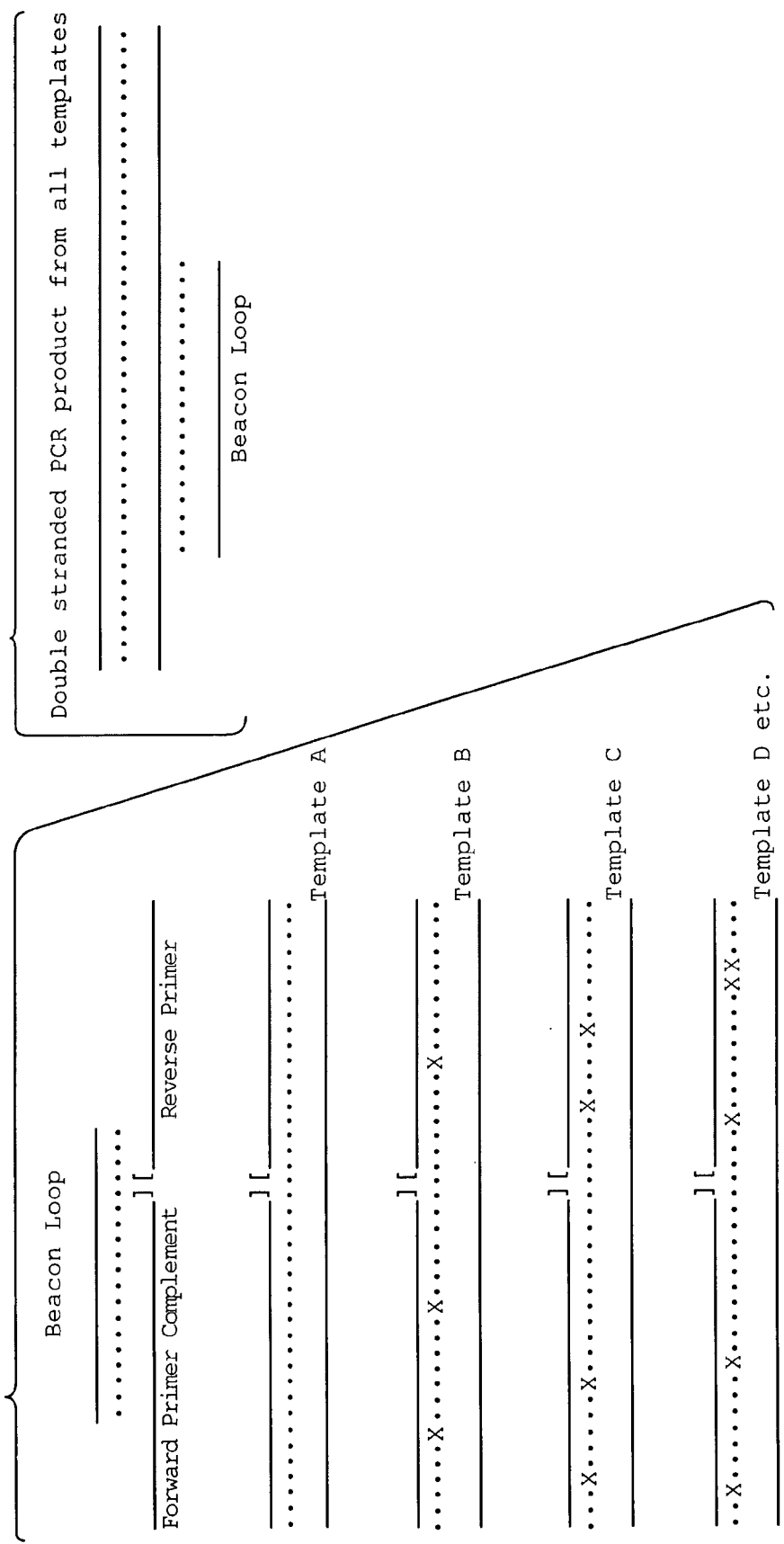

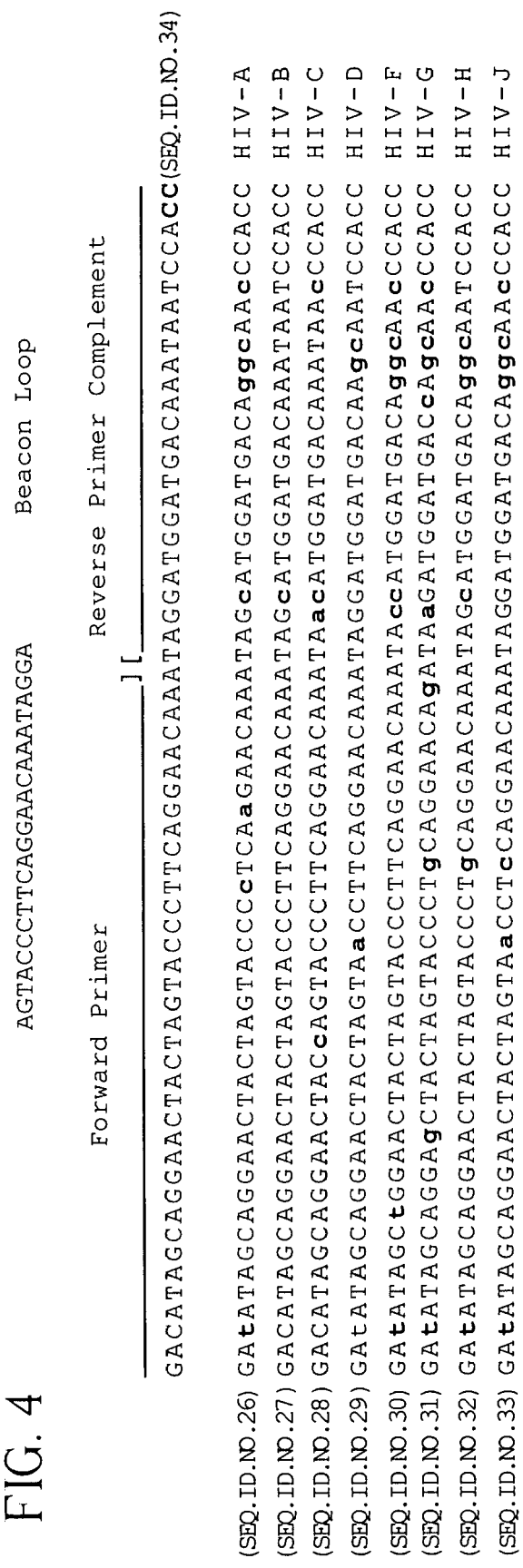

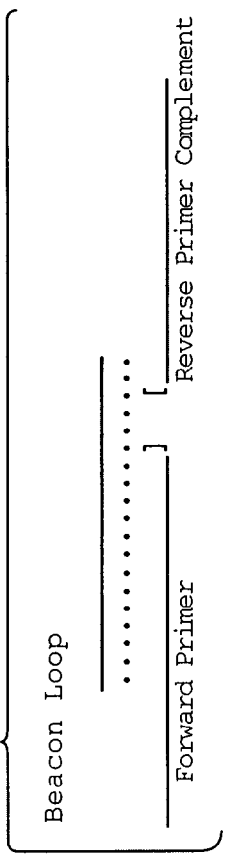
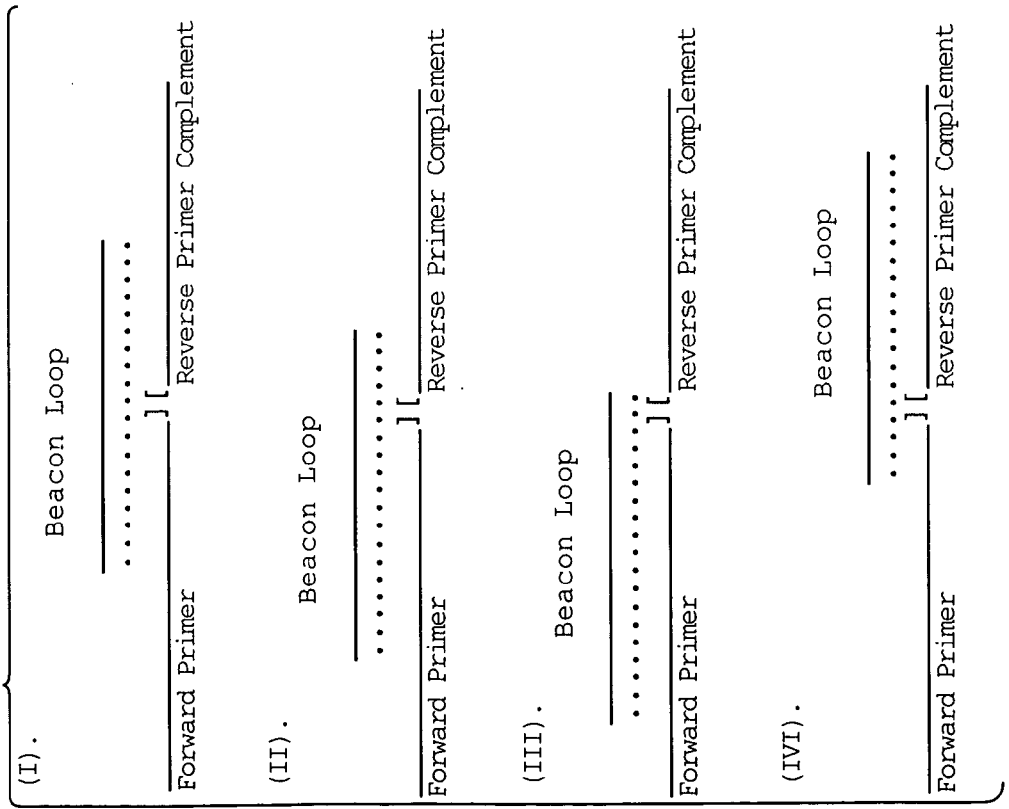
FIG. 5A
FIG. 5B

FIG. 6

```
                                                                               Beacon Loop
                                                              AAAAGGATAACTATGGGACCGG                              (SEQ.ID.NO.41)
          10        20        30        40        50        60        70        80        90       100
HIV/RT-1  AATGCTAAAATCATAATAGTACAGCTGAATGAATCTGTAGTAATTAATTGTACAAGACCCAACAATAATACAAGAAAAGGATAACTATGGGACCGGGGA (SEQ.ID.NO.37)
          110       120       130       140       150       160       170       180       190       200
          GAGTACTTTATACAACAGGAGAAATAATAGGAGAGATATAAGAGAGCACATTGTAACCTTAGTAGAGACAĞCATĞGAATAACACTTTAAAACAAATAGTTAC HIV/RT-10 AATGCTAAAATCATAATAGTACAGCTGAATGAATCTGTAGTAATTAATTGTACAGAGACCCAACAATAATACAAGAAAAGAATAACTATGGACCGGGGA  (SEQ.ID.NO.38)
          GAGTACTTTATACAACAGGAGAAATAATAGGAGAGATATAAGAGAGCACGTTGTAACCTTAGTAGAGCAGCATGGAATAACACTTTAAAACAGATAGTTAC HIV/38-1  AATGCTAAAATCATAATAGTACAGCTGAATGAATCTGTAGTAATTAATTGTACAGAGACCCAACAATAATACAAGAAAAGGGATACATATGGGACCGGGGA (SEQ.ID.NO.39)
          GAGTAtTTTATgCAACAGGAGAAATAATAGGAGAGATATAAGAcaAGCACATTGTAACCTTAGTgaAGCAGCATGAATAACACTTTAAAACAGATAGTTAC HIV/38-3  AATGCTAAAATCATAATACTACAGCTGAATGAATCTGTAGTAATTGTTCAAGACCCAACAATAACAAGAAAAGGGATACaaATGGGACCGGGGA         (SEQ.ID.NO.40)
          aAGTAtTTTATgCcACAcGACAAATAATAcAcAAGCACATTGTAACCTTAGTgaAGCAGCATGGAATAACACTTTAAAACAGATAGTTAC
```

(SEQ.ID.NO.42)
FAM-cgcacgAAAAGGATAACTATGGGACCGGcgtgcg-DABCYL

SEQUENCE LISTING

```
<160> NUMBER OF SEQ ID NOS: 17

<210> SEQ ID NO 1
<211> LENGTH: 20
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (1)..(20)
<223> OTHER INFORMATION: Nucleotide sequence encoding a primer

<400> SEQUENCE: 1
acgcagaaag cgtctagcca                                                    20

<210> SEQ ID NO 2
<211> LENGTH: 20
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(20)
<223> OTHER INFORMATION: Nucleotide sequence encoding a primer

<400> SEQUENCE: 2
gtactcaccg gttccgcaga                                                    20

<210> SEQ ID NO 3
<211> LENGTH: 29
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(29)
<223> OTHER INFORMATION: Nucleotide sequence encoding a primer

<400> SEQUENCE: 3
ccatggcgtt agtatgagtg tcgtgcagc                                          29

<210> SEQ ID NO 4
<211> LENGTH: 22
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(22)
<223> OTHER INFORMATION: Nucleotide sequence encoding a primer

<400> SEQUENCE: 4
cccgggaggg ggggtcctgg ag                                                 22

<210> SEQ ID NO 5
<211> LENGTH: 35
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (1)..(35)
```

<223> OTHER INFORMATION: Nucleotide sequence encoding a probe

<400> SEQUENCE: 5
ccgggcttag tatgagtgtc gtgcagcctg cccgg                                   35

<210> SEQ ID NO 6
<211> LENGTH: 30
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(30)
<223> OTHER INFORMATION: Nucleotide sequence encoding a primer

<400> SEQUENCE: 6
acaatacaag aaaaaggata actatgggac                                         30

<210> SEQ ID NO 7
<211> LENGTH: 30
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(30)
<223> OTHER INFORMATION: Nucleotide sequence encoding a primer

<400> SEQUENCE: 7
tttctcctgt tgtataaagt actctccccg                                         30

<210> SEQ ID NO 8
<211> LENGTH: 24
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(24)
<223> OTHER INFORMATION: Nucleotide sequence encoding a primer

<400> SEQUENCE: 8
taatagtaca gctgaatgaa tctg                                               24

<210> SEQ ID NO 9
<211> LENGTH: 22
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(22)
<223> OTHER INFORMATION: Nucleotide sequence encoding a primer

<400> SEQUENCE: 9
gttttaaagt gttattccat gc                                                 22

<210> SEQ ID NO 10
<211> LENGTH: 20
<212> TYPE: DNA
<213> ORGANISM: Artificial Sequence
<220> FEATURE:
<223> OTHER INFORMATION: primer
<220> FEATURE:
<221> NAME/KEY: misc_feature

```
<222> LOCATION: (1)..(20)
<223> OTHER INFORMATION: Nucleotide sequence encoding a primer

<400> SEQUENCE: 10
aaccaagggg aagtgacata                                              20

<210> SEQ ID NO 11
<211> LENGTH: 21
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(21)
<223> OTHER INFORMATION: Nucleotide sequence encoding a primer

<400> SEQUENCE: 11
atttctccta ctgggatagg t                                            21

<210> SEQ ID NO 12
<211> LENGTH: 30
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(30)
<223> OTHER INFORMATION: Nucleotide sequence encoding a primer

<400> SEQUENCE: 12
gaactactag taccctttcag gaacaaatag                                  30

<210> SEQ ID NO 13
<211> LENGTH: 27
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(27)
<223> OTHER INFORMATION: Nucleotide sequence encoding a primer

<400> SEQUENCE: 13
ggataggtgg attatttgtc atccatc                                      27

<210> SEQ ID NO 14
<211> LENGTH: 30
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (1)..(30)
<223> OTHER INFORMATION: Nucleotide sequence encoding a probe

<400> SEQUENCE: 14
cgccttaccc ttcaggaaca aatagaggcg                                   30

<210> SEQ ID NO 15
<211> LENGTH: 34
<212> TYPE: DNA
<213> ORGANISM: Artificial Sequence
<220> FEATURE:
<223> OTHER INFORMATION: primer
<220> FEATURE:
```

-continued

```
<221> NAME/KEY: misc_feature
<222> LOCATION: (1)..(34)
<223> OTHER INFORMATION: Nucleotide sequence encoding a primer

<400> SEQUENCE: 15
cagcagtaca aatggcagta ttcattcaca attt                              34

<210> SEQ ID NO 16
<211> LENGTH: 30
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(30)
<223> OTHER INFORMATION: Nucleotide sequence encoding a primer

<400> SEQUENCE: 16
ctgtatcccc caatcccccc ttttcttta                                   30

<210> SEQ ID NO 17
<211> LENGTH: 34
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (1)..(34)
<223> OTHER INFORMATION: Nucleotide sequence encoding a probe

<400> SEQUENCE: 17
cgcacggcag tattcattca ccaattttcg tgcg                              34
```

UNIVERSAL MULTI-VARIANT DETECTION SYSTEM

CROSS-REFERENCE TO RELATED APPLICATION

This application claims the benefit of U.S. Provisional Application No. 60/284,334, filed Apr. 17, 2001, which is incorporated herein by reference.

BACKGROUND OF THE INVENTION

The detection of closely related genetic variants is a significant challenge of analytical diagnostics. Pathogens such as, for example, viruses and bacteria, generally mutate frequently and form such genetic variants.

For example, the nucleic acid sequences of human immunodeficiency virus (HIV-1) having different origins, are different from each other. The different types of HIV-1 are divided into groups and subtypes. The major group M consists of ten currently identified subtypes, designated as subtypes A through H, J and K In addition to M-group viruses, two other groups, N and O, have been identified (Simon et al, 1998, Nature Med, 4:1032-1037). Within groups and subtypes, new strains of the virus are continuously being generated due to the error-prone nature of the HIV-1 replicative machinery.

Similarly, hepatitis C virus (HCV) does not exist as a homogeneous RNA population. Even within a single infected individual, numerous heterogeneous viral genomes (quasispecies) may co-exist. In addition, multiple genotypes of HCV have been identified on the basis of nucleotide sequence analysis of viral variants isolated from different geographic regions. There are currently six main HCV genotypes, classified numerically from 1 to 6. Genotypes are further subdivided according to subtype.

Due to this genetic variation of pathogens within a species, the range of diagnostic tests that provide reliable results are highly limited. Most detection methods currently available for detecting pathogens in a sample are based either on the detection of the pathogens' antigens, pathogen-induced antibodies, or the pathogens' intrinsic enzymes, e.g. intrinsic HIV reverse transcriptase. In addition to being inconvenient, such methods are frequently not very sensitive. For example, the method currently implemented by blood banks for screening of HIV-1 infection in blood donors is the detection of antibodies to virus proteins. This method fails to detect individuals in the early acute phase of the infection who have not yet developed diagnostic antibodies to the virus.

Screening methods that are based on the detection of nucleic acid sequences are sensitive and convenient. However, these tests may not always be reliable for detection of closely related genetic variants.

One of the currently available nucleic acid sequence-based detection methods utilizes molecular beacons (Tyagi and Kramer, 1996, Nat. Biotechnol., 14(3):303-308). Molecular beacons are single-stranded oligonucleotide probes that have a stem-loop structure. (See FIG. 1.) The loop portion of the molecule is a probe sequence complementary to a target nucleic acid molecule. The stem is formed by the annealing of complementary arm sequences on the ends of the probe sequence. A fluorescent moiety is attached to the end of one arm; and a quenching moiety is attached to the end of the other arm. The hybridization of the arms of the stem to each other keeps these two moieties in close proximity, causing the fluorescence of the fluorophore to be quenched by energy transfer (FIG. 1a). In the presence of the beacon's complementary DNA target, the loop structure hybridizes to the target, preventing the arms of the stem from remaining hybridized. The fluorophore and quencher are physically separated, and fluorescence is obtained (FIG. 1b).

Molecular beacons are currently used for real-time quantitative PCR. PCR primers are designed to amplify a specific segment of DNA, usually less than 200 base pairs in length. The beacon is typically designed so that its loop is complementary to a short (20-25 b.p.) region on one of the amplified DNA strands. The complementary region of these amplified DNA strands is the portion of these strands which has been added to the primers.

Molecular beacons are highly sequence-specific. In fact, one of the principle applications of this technology in recent years has been for allele discrimination or "molecular genotyping." The sensitivity of molecular beacons to sequence variation permits discrimination between even single nucleotide polymorphisms in a give target sequence (Tyagi et al, 1998, Nat. Biotechnol., 16(1):49-53; Kostrikis et al., 1998, Science, 279:5354:1228-9; Marras et al., 1999, Genet. Anal., 14(5-6)151-6; Tapp et al., 2000, Biotechniques, 28(4):732-8).

To date, this sensitivity to sequence variation has severely limited the application of molecular beacon technology to the diagnosis of viral infection. The molecular beacons cannot efficiently detect the variant sequences of DNA or RNA targets. For example, a beacon designed to recognize PCR product from HIV strain A may not recognize PCR product from HIV strain B. (See FIG. 2.)

Thus, the present technology would require several different beacons to allow for the detection of all the different genotypes of the virus. That is, even though some highly conserved regions of the genome of HIV-1 are known to exist, it is likely that several different beacons would be needed to detect all the known subtypes of this virus. Moreover, even with the use of several different beacons, other variants of HIV-1 that have not been identified may not be detected.

Thus, current technology does not provide a convenient or efficient diagnostic assay for detection of all related genetic variants of pathogens.

There is an urgent need for sensitive, convenient nucleic acid-based screening assays capable of detecting closely related genetic variants. For example, there is a need for assays capable of detecting viruses, bacteria and other pathogens, directly in contaminated blood. Such assays are needed to detect blood or plasma units from individuals in the early acute stages of a pathogen infection, i.e., before the individual has developed diagnostic antibodies to the virus.

Accordingly, one of the purposes of the present invention is to overcome the above limitations in the prior art by providing a convenient and efficient diagnostic assay for detection of multiple variants of a particular target nucleic acid molecule.

SUMMARY OF THE INVENTION

These and other objects, as will be apparent to those having ordinary skill in the art, have been met by providing a method to diagnostically detect the variants of a given pathogen, such as HIV, hepatitis C, hepatitis B (HBV), Parvovirus B19, etc., with the use of a single detection probe, i.e., a universal multi-variant detection system. In one embodiment, the single detection probe is a molecular beacon.

BRIEF DESCRIPTION OF FIGURES

FIG. 2: Conventional PCR using molecular beacons. PCR primers are designed to amplify a segment of viral RNA. A molecular beacon is designed so that its probe loop will hybridize to a segment of the PCR product which is internal to the two PCR primers. The beacon is capable of hybridizing to PCR product of virus strain A, but fails to detect PCR product of virus strain B because of mismatches in the target sequence (shown in lower case).

FIG. 3: A graphical illustration of one of the principles of the invention. (a.) Reverse and forward PCR primers (>30 b.p.) are designed to hybridize directly "nose-to-nose" to the target RNA (or DNA) and its complementary DNA strand respectively, such that the generated PCR product possesses no intervening sequence. The target-specific loop of the molecular beacon is designed to hybridize to the DNA sequence created by the junction of one of the primers and the other primer's complement. PCR primers will hybridize to target templates with mismatched residues, indicated by "X." Dotted lines indicate hybridization. (b.) The DNA sequence of the PCR product amplified from all templates is identical to the combined sequence of one of the primers and the other primer's complement. The molecular beacon is thus capable of hybridizing to PCR products generated from all templates.

FIG. 4: An example of the method. An amplification of different subtypes of HIV using "nose-to-nose" primers and a molecular beacon designed to recognize a sequence created by the junction of one of the primers and the other primer's complement. Mismatches between the sequence of the HIV variants and either the primers or beacon loop are shown in lower case boldface.

FIG. 5: Illustration of Variations on Primer Location. (A). The beacon loop can be designed to hybridize to an amplified sequence created equally by the two PCR primers as shown in (I). Alternatively, the beacon can be designed to hybridize "asymmetrically" to an amplified sequence created primarily by either the forward or reverse primer as shown in (II) to (IV). (B). In a further variation, the forward and reverse primers are separated by a nucleotide gap which corresponds to a highly conserved region of the viral genome.

FIG. 6: DNA sequence alignment of the V3 loop and flanking regions of four variants of HIV showing the positions of molecular beacon and primers for both conventional and "nose-to-nose" PCR (a). The protein coding strand of HIV/RT-1 is aligned with that of 3 other virus variants, HIV/RT-10, HIV-38-1 and HIV/38-3. Mismatches to the sequence of HIV/RT-1 and to the molecular beacon are shown in lower case in bold. The relative location of forward and reverse primers for conventional PCR are indicated by dotted (. . . .) and dashed (- - - -) lines respectively. The relative location of forward and reverse primers for nose-to-nose PCR are indicated by double (═) and solid (—) lines respectively. The location of the beacon probe is shown above the sequence. All primers and the beacon probe sequences are derived from the sequence of HIV/RT-1. (b). Structure of the molecular beacon. The probe loop is shown in upper case, the complementary stem nucleotides are shown in lower case. The fluorophore FAM is conjugated to the 5' end, the quencher DABCYL is conjugated to the 3' end.

DETAILED DESCRIPTION OF PREFERRED EMBODIMENTS

Figure 1B:
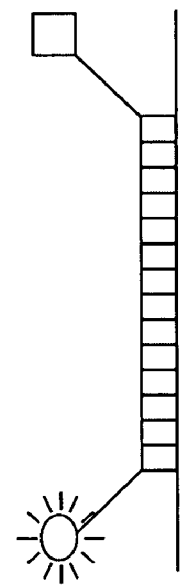
FIG. 1: A graphical illustration of a molecular beacon. At the appropriate annealing temperature the beacon will either: (A) in the absence of a complementary target sequence, form a stem loop structure causing the quenching moiety (□) to quench the luminescence of the reporter moiety (O); or (B) in the presence of a complementary target, bind to the target allowing the reporter to emit its signal.
Figure 1A:
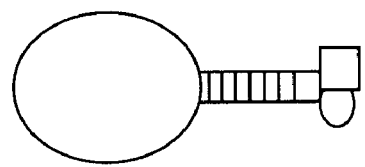

The present invention provides a method for determining the presence of a target nucleic acid molecule in a biological sample with the use of a single detection probe.

The method comprises the amplification of a target nucleic acid molecule by means of a primer extension chain reaction wherein the primers of the reaction are a set of "nose-to-nose" primers, including a forward and reverse primer, as described below. (See FIGS. 3 and 4.)

The target nucleic acid molecule is a nucleic acid molecule whose full or partial sequence is sufficiently known to make primer extension chain reaction primers. The target nucleic acid molecule can be single or double stranded.

The target nucleic acid molecule exists as a family of highly homologous sequences. These different sequences within a family are referred to as variants. The origin of the variants include, for example, gene mutations and polymorphisms.

Nucleic acid molecules which are known to have variants include, for example, viruses and bacteria. Examples of viruses include HIV, HCV, HBV and human parvovirus B19. Examples of bacteria include E. coli, S. pneumoniae, N. meningitidis, N. gonorrhoeae, M. Tuberculosis and Borrelia species (Lyme disease).

A biological sample from which a target nucleic acid molecule can be detected is any bodily fluid, cells or cellular debris. Examples of biological samples include blood, serum, semen, mucous or other bodily exudates.

The present invention can be used in any type of primer extension chain reaction that leads to the amplification of the target nucleic acid molecule or a subregion of this molecule. Amplification reactions include, for example, the polymerase chain reaction (PCR), including quantitative PCR; strand displacement amplification (SDA); transcription mediated amplification (TMA); and nucleic acid sequence based amplification (NASBA). NASBA amplifies RNA. NASBA is described in EP-A-0 329 822.

The conventional polymerase chain reaction (PCR) amplification process is well known in the art. Conditions suitable for carrying out a polymerase chain reaction are described in U.S. Pat. Nos. 4,683,195; 4,683,202; and 4,965,188. Commercial vendors, such as Perkin Elmer (Norwalk, Conn.), market PCR reagents and publish PCR protocols. A PCR amplification reaction mixture contains reagents necessary to carry out an amplification reaction. Typically, the mixture contains an agent for polymerization, such as thermostable DNA polymerase; deoxynucleoside 5' triphosphates (dNTP's); and a divalent metal cation in a suitable buffer.

Either DNA or RNA target sequences can be amplified by the methods of the present invention. In the case of PCR amplification of an RNA target, such as a viral genomic nucleic acid, the first step is the synthesis of a DNA copy (cDNA) of the target sequence. The reverse transcription can be carried out as a separate step or, preferably, in a combined reverse transcription-polymerase chain reaction (RT-PCR). The RT-PCR amplification of RNA is well known in the art and described in U.S. Pat. Nos. 5,322,770 and 5,310,652; Myers and Gelfand, 1991, Biochemistry 30(31):7661-7666; U.S. Pat. No. 5,527,669; Young et al., 1993, J. Clin. Microbiol. 31(4):882-886; and Young et ai., 1995, J. Clin. Microbiol. 33(3):654-657.

Primers are also included in the PCR reaction mixture. A primer is an oligonucleotide which, upon hybridizing to a template nucleic acid molecule, is capable of acting as a point of synthesis initiation during an amplification reaction. The template nucleic acid is the initial target nucleic acid molecules; and the amplification products generated from these molecules.

The length of the primers of the present invention is not critical. Typically the primer length ranges from about 15 to 55 nucleotides; more typically from about 20 to 45 nucleotides; and most typically from about 25 to 35 nucleotides. Preferably, the primers are constructed to be relatively long (>30 bases) to maximize the number of mismatches that can be tolerated between a primer and its template. A primer pair need not be of the same length. For example, the forward primer may be made up of twenty-nine nucleotides; while the reverse primer can be made up of twenty-two nucleotides.

The primers can be natural or synthetic. For PCR, the primers are preferably single-stranded oligodeoxyribonucleotides.

Hybridization refers to the formation of a duplex structure by two single-stranded nucleic acids due to complementary base pairing. Hybridization can occur between fully complementary nucleic acid strands or between "substantially complementary" nucleic acid strands that contain minor regions of mismatch, i.e. variants. The degree of mismatch tolerated can be controlled by suitable adjustment of the hybridization conditions. Conditions under which only fully complementary nucleic acid strands will hybridize are referred to as "stringent hybridization conditions" or "sequence-specific hybridization conditions." Stable duplexes of substantially complementary sequences can be achieved under less stringent hybridization conditions.

The hybridization conditions, i.e. stringency, of the present invention are set so that the primers can tolerate mismatches between the primers and the template, thereby allowing hybridization to all genetic variants. For example, the conditions could be set so that hybridization between a primer and a template can occur with up to 20% of the base pairs between the primer and the template mismatched.

Those skilled in the art of nucleic acid technology can determine suitable hybridization conditions empirically considering a number of variables including, for example, the length and base pair concentration of the oligonucleotides, ionic strength, the incidence of mismatched base pairs, and the temperature chosen for oligonucleotide annealing, following the guidance provided by the art (see, e.g., Sambrook et al., 1989, Molecular Cloning—A Laboratory Manual, Cold Spring Harbor Laboratory, Cold Spring Harbor, N.Y.; Wetmur, 1991, Critical Reviews in Biochem. and Mol. Biol. 26(3/4):227-259; Ausubel et al. (eds.), 1995, Current Protocols in Molecular Biology, (John Wiley & Sons, Inc., New York) at Unit 2.10; and U.S. Pat. No. 5,789,550.)

A detailed description of a cycle of a primer extension chain reaction of the present invention follows. The specific reaction described is PCR. However, other types of primer extension chain reactions can be used in the methods of this invention.

Figure 10:
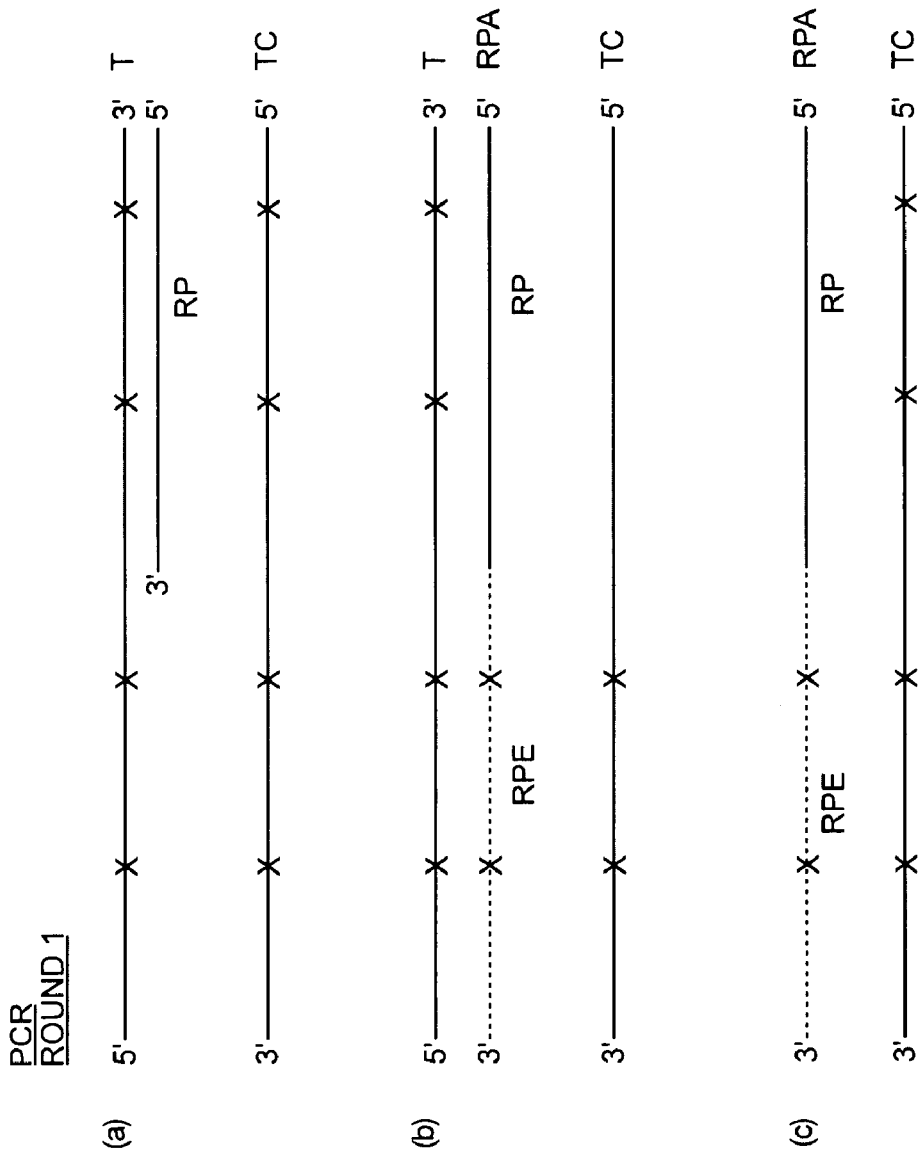
FIG. 10: A step-by-step illustration of an amplification reaction of the invention.
Figure 10:
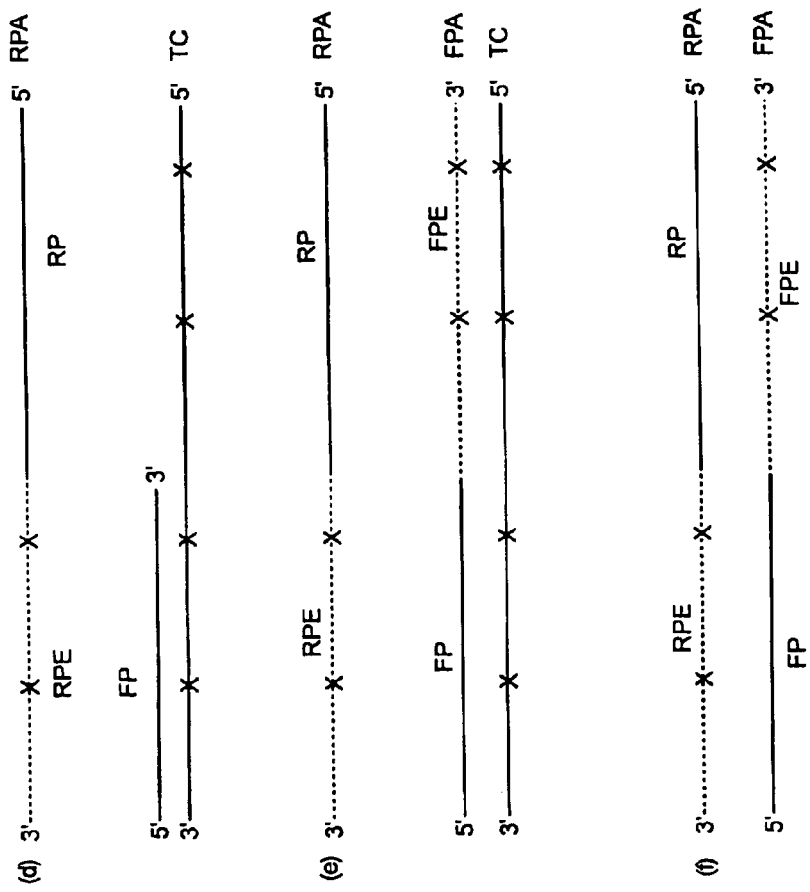
Figure 10:
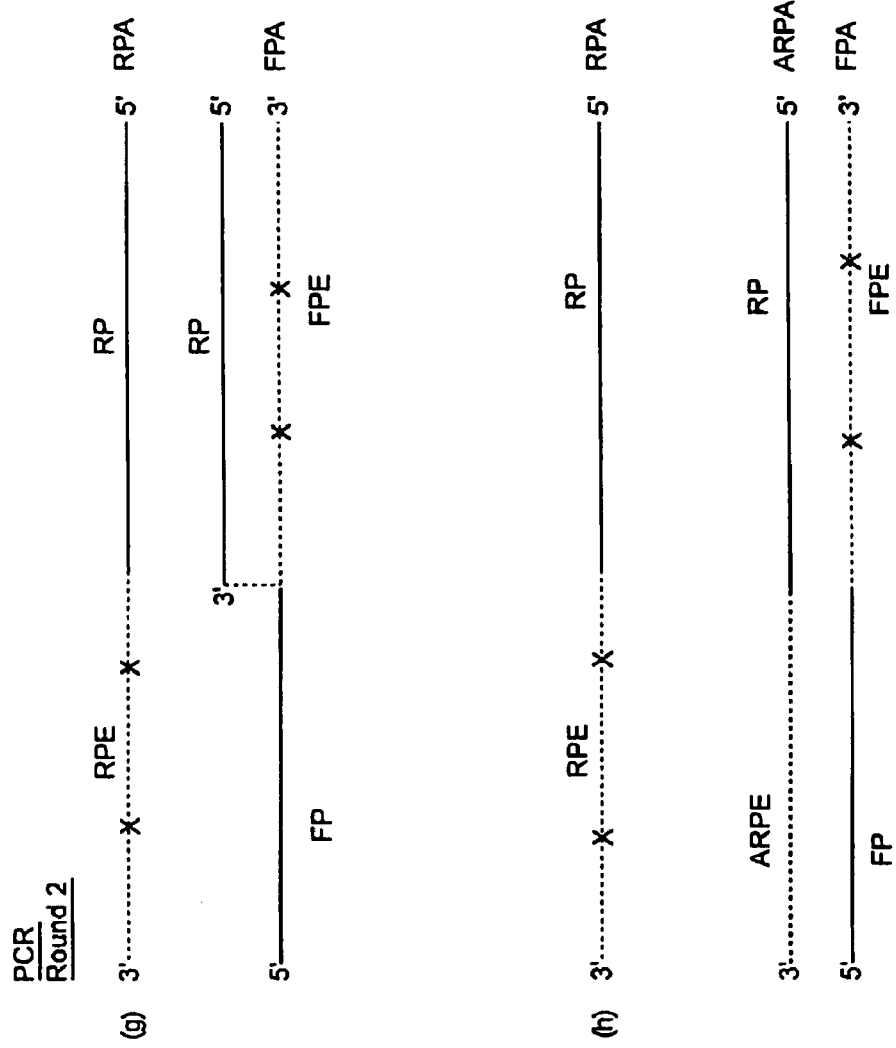
Figure 10:
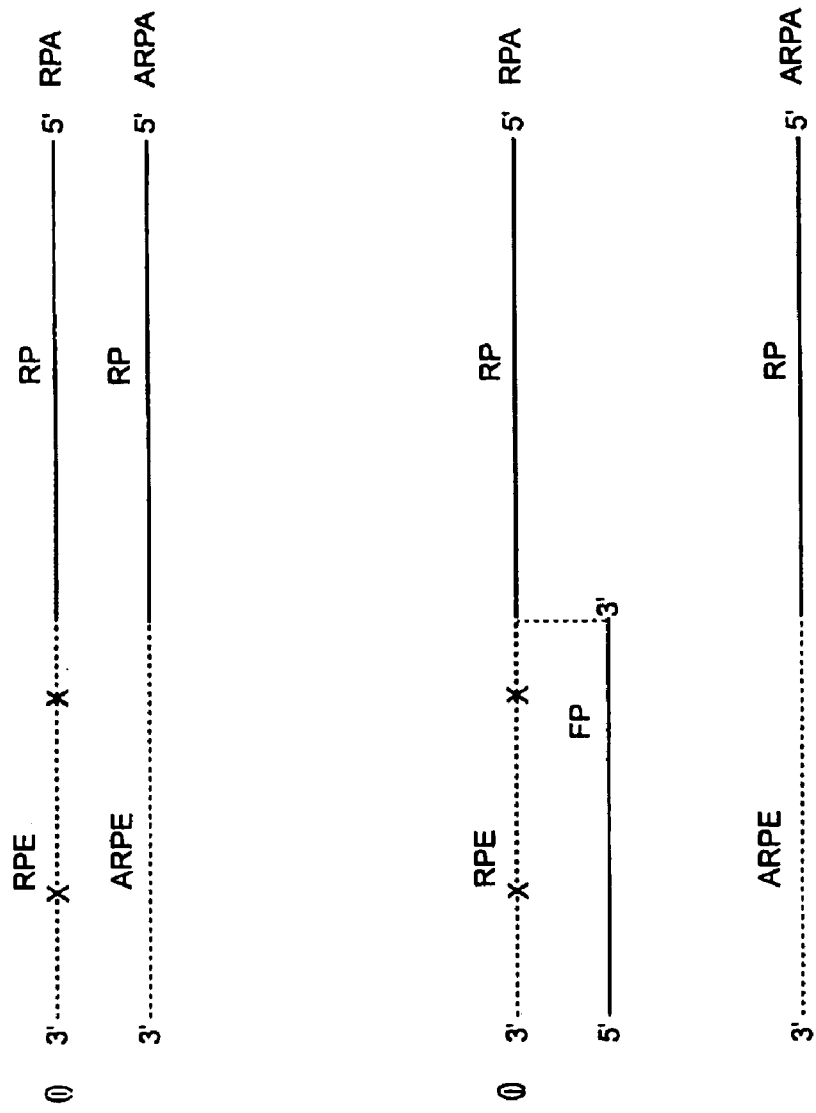
Figure 10:
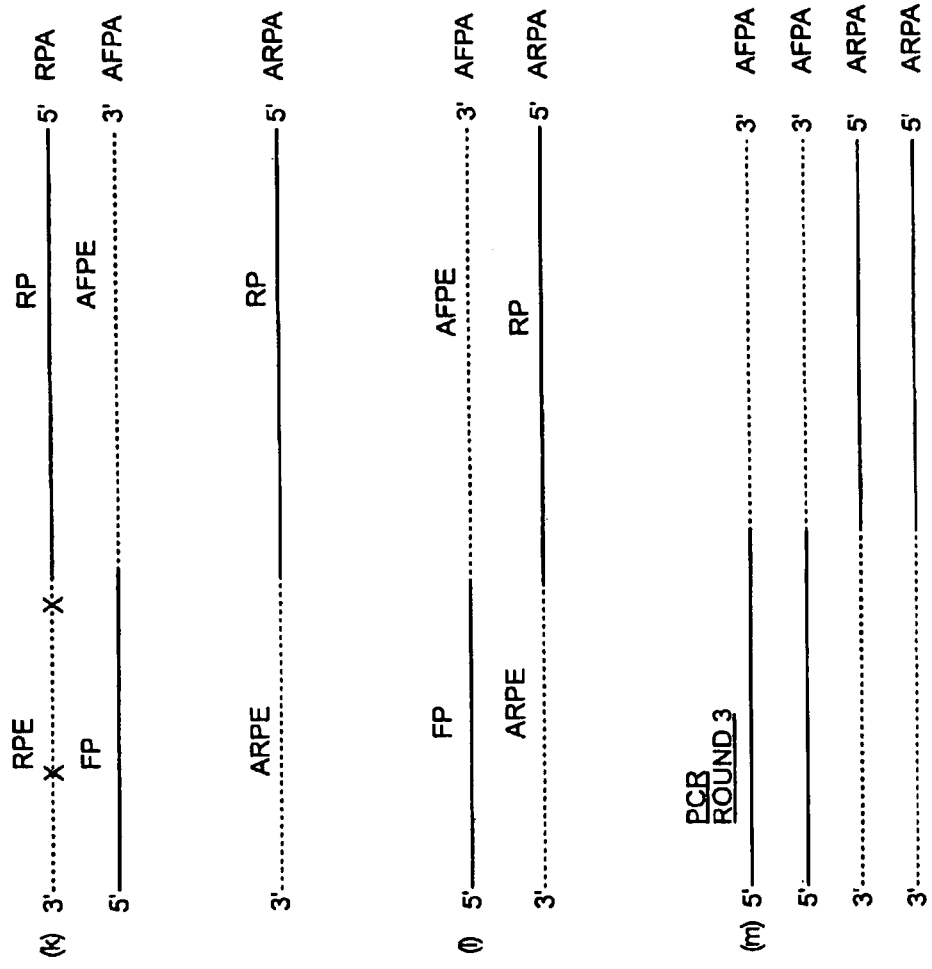

FIG. 10 gives a step-by-step illustration of an amplification reaction of the invention. The target nucleic acid molecule is represented by T. The X's within the target sequence represent sites of potential variations.

The target nucleic acid molecule can exist as a single-stranded molecule, or as part of a double stranded molecule. In the example illustrated in FIG. 10, the target nucleic acid molecule is double stranded. TC represents a nucleic acid molecule which is complementary to T.

As in conventional PCR, in each cycle of the amplification reaction any double-stranded nucleic acid molecules in a sample are rendered single-stranded by denaturation. Hybridization then takes place between the primers and the target nucleic acid molecules. FIG. 10(a) illustrates hybridization between a reverse primer (RP) and a target nucleic acid sequence (T).

As shown in FIG. 10(b), the reverse primers then are extended, using the target nucleic acid molecules as templates, to form reverse primer amplification products (RPA). The reverse primer amplification products (RPA) are comprised of the reverse primer (RP) joined to the reverse primer extension product (RPE). For the purposes of this specification, the reverse primer extension product is the nucleic acid segment which is added to the reverse primer.

As can be seen from FIG. 10(b), some of the variations (X) contained in the target sequence do not appear in the RPA. Specifically, the portion of the RPA which is made up of the RP does not contain variations.

As shown in FIG. 10(c), the reverse primer amplification products formed in step (b) are denatured from their templates.

The forward primers (FP) are hybridized to either: (i) nucleic acid molecules which are complementary to the target nucleic acid molecules (TC), if present; or (ii) the reverse primer amplification products (RPA). FIG. 10(d) illustrates the former embodiment. Nucleic acid molecules complementary to the target nucleic acid molecules, would be present if the target nucleic acid molecules were part of a double-stranded molecule.

The forward primers are then extended, using as templates the complementary nucleic acid molecules (TC) or using the reverse primer amplification products (RPA). FIG. 10(e) illustrates the former embodiment.

As shown in FIG. 10(e), the forward primers are extended to form forward primer amplification products (FPA). The forward primer amplification product (FPA) is comprised of the forward primer (FP) joined to the forward primer extension product (FPE). For the purposes of this specification, the forward primer extension product is the nucleic acid segment which is added to the forward primer.

As shown in FIG. 10(e), when compared with the target sequence, some of the variations (X) contained in the target sequence do not appear in the FPA. Specifically, the portion of the FPA which is made up of the FP does not contain variations.

As shown in FIG. 10(f), the forward primer amplification products formed in FIG. 10(e) are denatured from their templates.

As shown in FIG. 10(g), the reverse primers hybridize to the FPE portion of the FPA.

As shown in FIG. 10(h), the reverse primers are extended, using the FP portion of the FPA as templates, to form additional reverse primer amplification products (ARPA), wherein a reverse primer joined to an additional reverse primer extension product (ARPE) constitutes an ARPA.

As shown in FIG. 10(i), the ARPA products are denatured from their templates.

As shown in FIG. 10(j), the forward primers hybridize to the RPE portion of the RPA.

As shown in FIG. 10(k), the forward primers are extended, using the RP portion of the RPAs as templates, to form additional forward primer amplification products, wherein a forward primer joined to an additional forward primer extension product constitutes an AFPA.

As shown in FIG. 10(l), the AFPA products are denatured from their templates.

Steps (g) to (l) are repeated, using the additional reverse primer amplification products and the additional forward primer amplification products as templates for the reverse and forward primers, a sufficient number of times to produce a detectable quantity of additional reverse primer amplification product and/or of additional forward primer amplification product. Preferably, the steps are repeated using an automated cycling instrument. A sufficient number of times is at least about ten times, preferably at least about twenty times; more preferably at least about thirty times; and most preferably at least about forty times.

The present inventors have discovered advantages when the primers hybridize with the amplification products in a certain way, which the inventors refer to as "nose-to-nose."

As can be seen in FIG. 10(g), the sequence of the forward primer amplification products and the additional forward primer amplification products are such that the nucleotide at the 3' end of the reverse primer hybridizes with the nucleotide at the 5' end of the forward primer extension product or of the additional forward primer extension product.

Analogously, as can be seen in FIG. 10(j), the sequence of the reverse primer amplification products and the additional reverse primer amplification products are such that the nucleotide at the 3' end of the forward primer hybridizes with the nucleotide at the 5' end of the reverse primer extension product or of the additional reverse primer extension product.

FIG. 10 illustrates the primer extension chain reaction of only one variant. As indicated above, all variants of a family of pathogens can be amplified by the method of the invention.

The additional amplification products are identical, regardless of which variant they were generated from. Thus, in the example shown in FIG. 10, the additional reverse primer amplification products have the sequence of the reverse primer directly joined to the additional reverse primer extension product. The additional reverse primer extension product is complementary to the forward primer (the forward primer complement). See FIG. 10(h).

Analogously, the additional forward primer amplification products have the sequence of the forward primer directly joined to the additional forward primer extension product. The additional forward primer extension product is complementary to the reverse primer (reverse primer complement). See FIG. 10(k).

Therefore, all of the additional primer amplification products have sequences that are combinations of either the reverse primer and forward primer complement, or the reverse primer complement and the forward primer. Since the reverse and forward primers all have the same sequences, all of the additional primer amplification products have the same sequences. In other words, all of the potential variations have been eliminated.

In another embodiment, the sequence of the forward primer amplification products and the additional forward primer amplification products are such that the nucleotide at the 3' end of the reverse primer hybridizes with a nucleotide separated from the nucleotide at the 5' end of the forward primer extension product or of the additional forward primer extension product by a gap of nucleotides. Analogously, the sequence of the reverse primer amplification products and the additional reverse primer amplification products are such that the nucleotide at the 3' end of the forward primer hybridizes with a nucleotide separated from the nucleotide at the 5' end of the reverse primer extension product or of the additional reverse primer extension product by a gap of nucleotides.

In both cases, the gap comprises a sequence known to be highly conserved. Highly conserved regions of the genomes of viruses and bacteria are known. For example, in the published sequence of HCV, short stretches of nucleic acids in the 5' non-coding region of the viral genome are known to be highly conserved between HCV genotypes (Okamoto et al., *J. Gen. Virol.*, 1991,2697-2704; Smith et al., *J. Gen. Virol.*, 1995, 76:1749-1761; Simmonds et al., *J. Gen. Virol.*, 1993, 74: 2391-2399).

The gap preferably contains no more than five nucleotides. If the gap contains two to five nucleotides, one or two of the nucleotides can be mismatched and still hybridize with the probe sequence. If the gap contains one nucleotide, this nucleotide can be a mismatch. Preferably, there are no mismatches.

Once the amplification reaction has been completed, the presence of the additional reverse primer amplification products or the additional forward primer amplification products is detected by methods known in the art.

Preferably, the method of detection is based on the detection of the nucleic acid sequences of the additional reverse primer amplification products or of the additional forward primer amplification products. The detection probe used in such a method comprises a sequence that is capable of hybridizing with the additional reverse primer amplification products or with the additional forward primer amplification products. Since these amplification products are identical, only one detection probe is needed to reliably detect all the amplification products.

Additionally, the identity of the amplification products allows for stringent hybridization conditions to be used during the hybridization required for detection. The use of stringent conditions leads to more reliable results by reducing the possibility of false positives from coincidentally similar non-target sequences.

The detection probe can be DNA, RNA, or combinations thereof. Modified nucleotides may be included, for example peptide nucleic acid (PNA), nitropyrole-based nucleotides, or 2'-O-methylribonucleotides. The nucleosides of the nucleic acid or modified nucleic acid molecules may be linked in the usual manner, i.e. through phosphate linkages. Alternatively, the nucleosides may be linked through modified linkages, for example phosphorothioates.

In one embodiment, the probe sequence hybridizes over the junction in the amplification products. That is, the probe sequence hybridizes to a portion of both the FP sequence and the AFPE sequence of the AFPA; or the probe sequence hybridizes to a portion of both the RP sequence and the ARPE sequence of the ARPA.

In this embodiment, the probe sequence is comprised of the nucleotide sequence of a segment of one of the primers and the nucleotide sequence of a segment which is complementary to the other primer. More specifically, the probe sequence comprises either: (i) the nucleotide sequence of a segment of the forward primer and the nucleotide sequence of a segment which is complementary to the reverse primer; or (ii) the nucleotide sequence of a segment of the reverse primer and the nucleotide sequence of a segment which is complementary to the forward primer. The probe sequence can comprise either whole or partial sequences of the primer, and the other primer's complement.

The probe sequence can be made up of equal portions of the nucleotide sequence of one of the primers and the nucleotide sequence of the other primer's complement. In such a case, the probe sequence will "hybridize symmetrically" to the amplification products. (See FIG. 5A(I).)

Preferably, for improved sensitivity, the probe sequence can be designed to "hybridize asymmetrically" to the amplification products. In particular, the probe sequence can be made up of unequal portions of the nucleotide sequence of one of the primers and the nucleotide sequence of the other primer's complement. (See FIG. 5A(II-IV.) For example, about 60% to about 99% of the probe sequence comprises the nucleotide sequence of one of the primers. The remainder of the probe sequence (e.g., about 1% to about 40%) comprises the nucleotide sequence of the complement of the other primer. More preferably, the percentage of the probe sequence which corresponds to the sequence of one of the primers is from about 80% to about 97%.

Where the sequence of the additional amplification products contains a segment of one of the primers directly adjoined to a segment of the other primer's complement, the probe sequence can be designed to hybridize exactly to all, or a portion of, the additional amplification products.

Where the additional amplification products contain an intervening gap, the gap is preferably a known sequence so that the probe sequence can be designed to be fully complementary to the gap. However, a probe sequence can hybridize to additional amplification products which contain a certain number of mismatched residues in the gap, as described above.

Instead of hybridizing over the junction, the probe sequence can also hybridize exclusively with the segment of the additional amplification product that is complementary to a primer. Accordingly, in this embodiment, the probe sequence is comprised of either: the nucleotide sequence of a segment of the forward primer, and not the nucleotide sequence of a segment which is complementary to the reverse primer, or the nucleotide sequence of a segment of the reverse primer, and not the nucleotide sequence of a segment which is complementary to the forward primer.

In one embodiment of the primer extension chain reactions of the invention, equal concentrations of the forward primer and reverse primer are used. In this embodiment, the concentrations are said to be symmetric.

In a preferred embodiment, "asymmetric concentrations" of the forward and reverse primers are used. In particular, for improved sensitivity, the primer whose nucleotide sequence makes up part of the probe sequence is provided in a lower concentration in the sample as compared with the other primer. "Asymmetric concentrations" of primers are particularly preferred if the probe sequences "hybridize asymmetrically" with the additional amplification products; or hybridize exclusively with the segment of the additional amplification products that is complementary to a primer.

For example, if the probe sequence comprises a segment of the nucleotide sequence of the forward primer, then the molar ratio of the forward primer to the reverse primer (FP:RP) is about 1:5 to about 1:20. Analogously, if the probe sequence comprises a segment of the nucleotide sequence of the reverse primer, then the molar ratio of the reverse primer to the forward primer (RP:FP) is about 1:5 to about 1:20, more preferably from about 1:6 to about 1:15, and most preferably about 1:10.

After the amplification reaction has taken place in the biological sample a sufficient number of times, the detection probe is contacted with the sample. The probe sequence of the detection probe hybridizes with any additional amplification products that may be present in the sample. If the probe sequence comprises the nucleotide sequence of a segment of the forward primer (exclusively or further comprising the nucleotide sequence of a segment of the reverse primer complement), the probe sequence will hybridize with the additional reverse primer amplification products. Analogously, if the probe sequence comprises the nucleotide sequence of a segment of the reverse primer (exclusively or further comprising and the nucleotide sequence of a segment of the forward primer complement), the probe sequence will hybridize with the additional forward primer amplification products.

In a preferred embodiment, the detection probe is a self-altering signal-generating probe. This probe comprises a first nucleic acid sequence; a second nucleic acid sequence complementary to the first nucleic acid sequence; and a probe sequence which connects the first nucleic acid sequence with the second nucleic acid sequence. The first nucleic acid sequence is attached to a reporter moiety which is capable of generating a detectable signal. The second nucleic acid sequence is attached to an interactive moiety which is capable of altering the signal generated by the reporter moiety when the reporter moiety and the interactive moiety are in sufficient proximity to each other. For example, when the first and the second nucleic acid sequences are hybridized to one another, known as the "closed conformation," the reporter moiety is brought into proximity with the interactive moiety. Therefore, the signal is altered. Altering the signal includes decreasing, i.e. quenching; increasing; or otherwise changing the signal, such as the intensity or wavelength of the signal. Quenching the signal includes reducing or eliminating the signal.

The reporter and interactive moieties can be attached at any point on the detection probe which would allow for the alteration by the interactive moiety of a signal generated by the reporter moiety for detection of the additional amplification products. In the preferred embodiment, the reporter moiety and the interactive moiety are attached at the distal termini of the self-altering signal-generating probe.

In the absence of additional amplification products, the detection probe is in the closed conformation. The reporter and interactive moieties are in proximity to each other. Therefore, the signal is altered.

Upon hybridization of the probe sequence with the additional reverse primer amplification product or with the additional forward primer amplification product, the first and second nucleic acid sequences of the detection probe become denatured. This is known as the "open conformation."

Upon denaturation, the interactive moiety is no longer in sufficient proximity to the reporter moiety to alter the signal. The difference between the altered signal and the unaltered signal is detected. When the interactive moiety quenches the signal, for example, the unaltered signal is increased; or if the quenching was complete, a signal is generated.

The strength of the hybridization formed between the first and second nucleic acids (i.e., the stem of the probe) can be adjusted by routine experimentation to achieve proper functioning. For example, the strength is a function of the length of the nucleotides. The lengths of the first and second nucleic acid sequences are preferably in the range of about 3 to 15, more preferably about 4 to 7 nucleotides. In addition to length, the strength of the hybridization can be reduced by decreasing the G-C content and by inserting destabilizing mismatches in the nucleotides.

The length of the probe sequence is not critical. However, the length cannot be so short that effective binding with the additional amplification products is not achieved. Additionally, the length cannot be so great that separation of the reporter moiety and the interactive moiety is not achieved despite the probe sequence being hybridized with the products. Preferably, the probe sequence comprises from about ten to about thirty nucleotides; more preferably from about eighteen to about twenty-four nucleotides; and most preferably from about nineteen to about twenty-two nucleotides. The probes can be free in solution, or they can be tethered to a solid surface.

Any concentration of the detection probe that produces a detectable signal can be used in the methods. For example, the concentration of the detection probe can be provided in the sample at about the same concentration as one, or both, of the primers.

Preferably, the concentration of the detection probe is greater than the concentrations of the primers. In this manner, the detection probe is favored in the competition between the primer, whose nucleic acid sequence is part of the probe sequence, and the detection probe for the additional amplification products. This increase in the concentration of the detection probe is particularly preferred when the probe sequence "hybridizes asymmetrically" to the amplification products, or hybridizes exclusively to the portion of the additional amplification products which are complementary to a primer, as described above. For example, the detection probe can be provided at a concentration which is from about 1.3 to about 5 times; more preferably from about 1.5 to about 3 times; and most preferably about twice as great as the concentration of the primer whose nucleic acid sequence is not part of the probe sequence.

In a preferred embodiment, the probe sequence is made up of, for example, at least 65% of the sequence of the forward primer; the forward primer is provided in a concentration which is about ten times less than the concentration of the reverse primer, and the detection probe is provided in a concentration which is about twice as great as the reverse primer.

An unaltered signal generated by the reporter moiety is an indication that the target nucleic acid molecule is present in the sample. The level of the detectable unaltered signal generated by the probe is proportional to the quantity of the target nucleic acid molecules in the sample.

The detectable signal of the detection probes can be any kind of signal including, for example, a luminescent signal, a color dye signal, or a radioactive signal. In the preferred embodiment, the detectable signal is a luminescent signal. The luminescent signal can be a fluorescent signal or chemiluminescent signal.

In one embodiment, the reporter and interactive moieties of this invention constitute a "FRET" pair. (Selvin, P. R., "Fluorescence Resonance Energy Transfer," Methods in Enzymology 246: 300-335 (1995).) FRET pairs rely on energy transfer for signal generation. The reporter moiety absorbs energy at a first wavelength and emits a second, longer wavelength. The interactive moiety absorbs some or most of the emitted energy to the degree the interactive moiety's spectrum overlaps the emission spectrum. If the interactive moiety is a quencher, the quencher releases the energy as heat. If the interactive moiety is a fluorophore, the interactive moiety re-emits at a third, still longer wavelength. The mechanism of FRET-pair interaction requires that the absorption spectrum of the interactive moiety overlaps the emission spectrum of the reporter moiety. The efficiency of FRET interaction is linearly proportional to that overlap.

In another embodiment, the reporter moiety and interactive moiety are a non-FRET pair. In particular, the interactive moiety need not have an absorption spectrum that overlaps the emission spectrum of the reporter moiety. That is, the absorption wavelength of the interactive moiety can be shorter than the reporter's excitation maximum and emission wavelength. Non-FRET pairs are described in U.S. Pat. No. 6,150,097 and are incorporated herein by reference. The detectable signal in a non-FRET pair can be a change in the absorption spectra, as an alternative to a change in luminescence.

Preferably, the reporter moieties of the detection probes used in the methods of this invention are fluorophores. The fluorophore can be a xanthene dye, a cyanine dye, a dansyl derivative, EDANS, coumarin, such as 3-phenyl-7-isocyanatocoumarin, Lucifer yellow, BODIPY, Cy3, Cy5, Cy7, Texas red, erythrosine, naphthylamine, Oregon green, ALEXA fluor dyes, acridines, such as 9-isothiocyanatoacridine and acridine orange, N-(p-(2-benzoxazolyl)phenyl)maleimide, benzoxadiazoles, stilbenes, and pyrenes.

The xanthene dye can be fluorescein or rhodamine. Preferably, the fluorescein is 5-carboxyfluorescein (5-FAM); 6-carboxyfluorescein (6-FAM); 2',4',1,4,-tetrachlorofluorescein (TET); 2',4',5',7',1,4-hexachlorofluorescein (HEX); eosin; calcium green; fluorescein isothiocyanate (FITC); or NED. Preferably, the rhodamine dye is tetramethyl-6-carboxyrhodamine (TAMRA); tetrapropano-6-carboxyrhodamine (ROX); 2',7'dimethoxy-4',5'-dichloro-6-carboxyrhodamine.(JOE) or tetramethylrhodamine (TMR). Many suitable forms of these compounds are commercially available with various substituents on their xanthene rings which can be used as the site for bonding or as the bonding functionality for attachment to an oligonucleotide.

The fluorophore can also be a naphthylamine compound. The naphthylamine compounds have an amino group in the alpha or beta position. Included among such naphthylamino compounds are 1-dimethylaminonaphthyl-5-sulfonate, 1-anilino-8-naphthalene sulfonate and 2-p-toluidinyl-6-naphthalene sulfonate.

The fluorophore can also be a combination fluorophore. An example of a combination fluorophore are fluorescein-rhodamine dimers, described, for example, by Lee et al. (1997), Nucleic Acids Research 25:2816. Fluorophores may be chosen to absorb and emit in the visible spectrum or outside the visible spectrum, such as in the ultraviolet or infrared ranges.

Preferably, the interactive moieties of the detection probes used in the methods of this invention are quenchers. The quencher can be DABCYL, anthroquinone, nitrothiazole, nitroimidazole or malachite green. Variants of DABCYL, such as DABSYL, DABMI or methyl red, are also suitable. Also the asymmetric cyanine dye compounds disclosed in U.S. Pat. No. 6,080,868 can be used as the quenching moiety; and are incorporated by reference.

Additionally, fluorophores can also be used as the quenchers. For example, fluorophores that do not fluoresce in the detection range when the probe is in the open conformation can quench fluorescence when in proximity with certain other fluorophores.

An example of a self-altering signal-generating probe is a molecular beacon probe. The loop of a molecular beacon probe corresponds to the probe sequence, as described above. Nucleotide sequences, referred to as "arms," correspond to the first and second nucleotide sequences, as described above. Molecular beacon probes are described in U.S. Pat. No. 5,925,517; PCT application WO95/13399; PCT application WO97/39008; and Tyagi and Kramer (1996) Nature Biotechnology 14:303; and are incorporated herein by reference.

Additionally, the molecular beacon probes can be modified in any manner which allows for detection of the amplification products. Modified probes include, for example, the "wavelength-shifting" molecular beacon probes described in U.S. Pat. No. 6,037,130; and incorporated herein by reference. In particular, these modified probes have the basic molecular beacon probe structure, namely, a loop; stem duplex; a quencher on one end; and a reporter moiety, typically a fluorophore, opposite the quencher on the other end. The reporter is referred to as the "harvester reporter." The modification of the probe is that the probe includes an extension of several nucleotides past the "harvester reporter." The extension terminates in a nucleotide that is linked to an "emitter reporter," typically another fluorophore. In the presence of the target nucleic acid molecule, the quencher separates from the reporters. In this open conformation the "harvester reporter" absorbs energy from the excitation source but transfers a significant portion of the energy, in some constructions the great majority of the energy, to the "emitter reporter," which receives the transferred energy and emits it at its characteristic, longer wavelength.

In another embodiment, the detection probe includes a pair of oligodeoxynucleotides complementary to contiguous regions of the additional amplification products. (Cardullo et al. (1988), Proc. Nat'l. Acad. Sci. 85: 8790-8794 and Heller et al. EP 00 70685. One oligodeoxynucleotide contains the reporter moiety on its 5' end, and the other oligodeoxynucleotide contains the interactive moiety on its 3' end. When the probe is hybridized to the target sequence, the two moieties are brought very close to each other. When the sample is stimulated by light of an appropriate frequency, fluorescence resonance energy transfer from one moiety to the other occurs, producing a measurable change in spectral response from the moieties, thus signaling the presence of targets.

In yet another embodiment, the detection probe includes a pair of oligodeoxynucleotides. The pair is complementary to one another. Also, one of the pair has the sequence of the target nucleic acid molecule; and the other of the pair has the sequence which is complementary to the target nucleic acid molecule. (Morrison and Stols, "Sensitive Fluorescence-Based Thermodynamic and Kinetic Measurements of DNA Hybridization in Solution,"Biochemistry 32: 309-3104 (1993) and Morrison EP 0 232 967 A2, claiming priority of U.S. application Ser. No. 817,841, filed Jan. 10, 1986.) Each oligodeoxynucleotide of the probe includes a reporter moiety conjugated to its 3' end and an interactive moiety conjugated to its 5' end. When the two oligonucleotides of the probe are annealed to each other, the reporter moiety of each is held in close proximity to the interactive moiety of the other. With the probe in this conformation, if the reporter is then stimulated by light of an appropriate wavelength, the signal is altered, preferably quenched, by the interactive moiety. However, when either probe molecule is bound to a target, the altering effect of the complementary oligodeoxynucleotide of the probe is absent. In this conformation a signal is generated. The oligodeoxynucleotides of the probe are too long to self-quench by FRET when in the target-bound conformation.

The signal generated by the detection probe can be detected and measured by any means known in the art which provides reliable detection and measurement.

For example, the ABI-7700 (manufactured by Applied Biosystems, Inc. in Foster City, Calif.) is adapted for measuring signal emission, typically fluorescence emissions. The ABI 7700 uses fiber optics connected with each well in a 96-well amplification reaction tube arrangement. The instrument includes a laser for exciting the reporter moieties and is capable of measuring the signal intensity, typically fluorescence spectra intensity, from each tube with continuous monitoring during amplification.

The additional amplification products can be quantified by endpoint and real-time measurements. In an end-point mode, the signal measurement is performed after the amplification reaction is complete, e.g., after all or substantially all of the cycles of an amplification reaction have been completed. In a real-time mode, signal measurement is performed multiple times during the amplification reaction, e.g., after each thermocycle of an amplification reaction. The real-time mode is preferred when a quantitative measure of the initial amount of target nucleic acid molecule is required, e.g., the copy-number of viral or bacterial nucleic acids present in a sample.

The absolute amount of a target nucleic acid molecule present in a test sample prior to amplification can be determined using a standard curve. For example, a standard curve can be generated from the results obtained from a series of parallel primer extension chain reactions. These parallel reactions are performed on a series of standard samples that contain a known amount of a nucleic acid molecule which is similar to the target nucleic acid molecule. A series of about five to about twenty standard samples of different known amounts are used. The parallel extension reactions use the same reaction conditions and reagents as used in the extension reaction of the target nucleic acid molecule.

In each parallel reaction, the increase in signal intensity as compared with the baseline signal intensity (delta Rn) is measured at the annealing temperature for each amplification cycle. The baseline value is the magnitude of the signal detected prior to the formation of the additional amplification products. Threshold values (Ct) are calculated for each reaction. Ct is the amplification cycle number at which the generated signal intensity is distinguishable from the baseline signal intensity. The starting quantity of the nucleic acid in each standard sample can be plotted against its corresponding Ct value. This plot is the standard curve.

In general, the threshold value must be high enough to be statistically different from the baseline value but below the signal obtained for the saturation phenomenon associated with amplification reactions. Typically, the threshold value is set at about ten standard deviations above the mean baseline signal intensity. (See, for example, Heid, et al. Genome Research 6:986-994 (1996)).

Figure 9A:
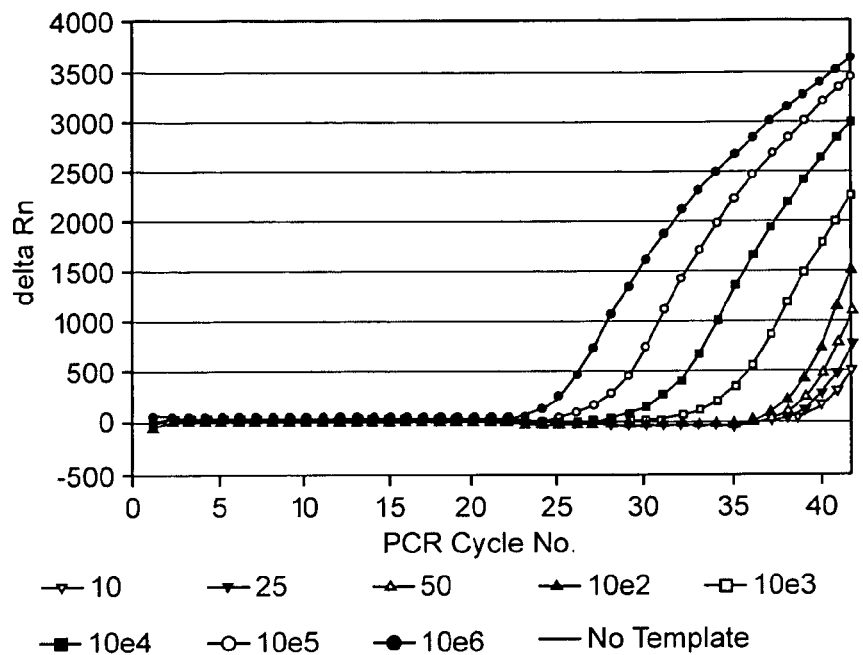
FIG. 9: An example of a standard curve for quantitation of HCV RNA using "nose-to-nose" RT-PCR with product detection using a molecular beacon. (a). "Nose-to-Nose" RT-PCR for HCV RNA was performed with an input of 0, 10, 25, 50, 100, $10^3$, $10^4$, $10^5$ or $10^6$ synthetic HCV RNA molecules per RT-PCR reaction. Change in fluorescence (delta Rn) was measured at the annealing temperature for each PCR cycle in the ABI 7700 Sequence Detector. Threshold values (Ct) were then calculated using software provided with the instrument. (b). The RNA copy number of each standard sample is plotted against its Ct value (●). The Ct values for unknown test samples (o) are plotted against the standard curve and RNA copy number is extrapolated from the X-axis.
Figure 9B:
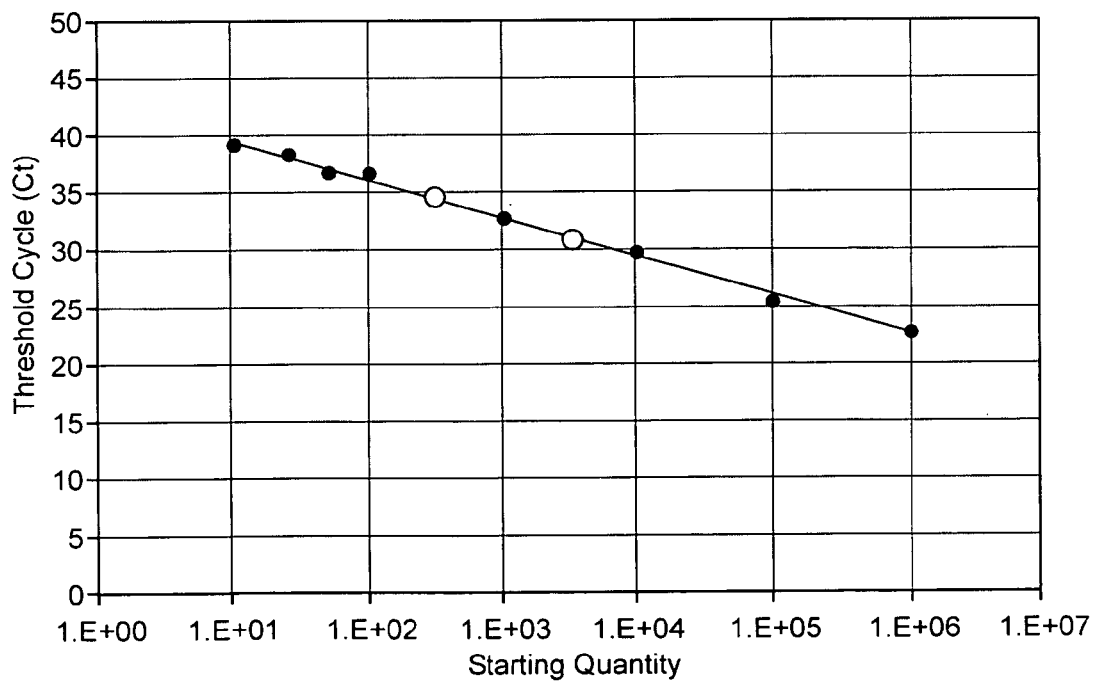

The Ct value for the sample including the target nucleic acid molecule is also calculated. This Ct value can be plotted against the standard curve. Using the standard curve, the amount of the target nucleic acid molecule in the test sample can then be quantified by extrapolation. FIG. 9 illustrates this method of PCR target quantitation (in the case of HCV RNA) using the "nose-to-nose" PCR primers and reaction conditions described in the Example below.

Computer software provided with detection instruments, for example the ABI 7700, is capable of recording the signal intensity over the course of an amplification. These recorded values can be used to calculate the increase in signal intensity on a continuous basis. Although the ABI 7700 instrument is typically used to monitor fluorescence, the Ct values need not be determined from fluorescence measurements. Ct values could be determined from measurements of a variety of different types of signals.

The present invention also relates to kits, multicontainer units comprising useful components for practicing the present method. The kit comprises a set of nose-to-nose primers for the amplification of the variants of a particular pathogen; and a probe, such as the self-altering signal-emitting probes described above. In some cases, the probes are fixed to an appropriate support membrane. Other optional components of the kit include, for example, an agent to catalyze the synthesis of primer extension products, the substrate nucleoside triphosphates, the appropriate buffers for amplification and/or hybridization reactions, a nucleic acid reference standard to permit quantitation of template molecules in test samples, and instructions for carrying out the present method.

EXAMPLES

The examples of the present invention presented below are provided only for illustrative purposes and not to limit the scope of the invention. Numerous embodiments of the invention within the scope of the claims that follow the examples will be apparent to those of ordinary skill in the art from reading the foregoing text and following examples.

Detection of HCV Variants

A comparison was made of three different methods for nucleic acid-based detection of eight strains of HCV which are prototypes for the main HCV genotypes and subtypes. The four detection methods used were: (A.) The nose-to-nose beacon RT-PCR of the present invention, (B.) Conventional beacon RT-PCR, and (C.) The COBAS AMPLICOR HCV MONITOR Test Version 2.0 (COBAS HCM-2; Roche Diagnostic Systems Inc, Branchburg, N.J.). The COBAS HCM-2, which is an RT-PCR-based assay, was carried out according to the manufacturers' instructions. Conventional beacon RT-PCR and "nose-to-nose" beacon RT-PCR were carried out as follows:

PCR primers were designed to amplify a segment of the 5' non-coding region of the HCV genomic RNA. The nucleic acid sequence of this region of the genome is relatively highly conserved between HCV genotypes and subtypes.

Conventional primers for beacon PCR were designed to amplify a 101 b.p. segment of DNA corresponding to nucleotides 66 to 166 of the published sequence of HCV-H [Inchauspe et al, Proc Natl Acad Sci (USA), 88:10292-10296, 1991; Genbank M67463]. The intervening gap between the two conventional RT-PCR primers is 61 b.p. in length. The primers are as follows:

```
Forward    5'-ACGCAGAAAGCGTCTAGCCA-3';   (SEQ ID NO:1)
primer:

Reverse    5'-GTACTCACCGGTTCCGCAGA-3'.   (SEQ ID NO:2)
primer:
```

The primers for "nose-to-nose" RT-PCR of the present invention were designed such that there is no intervening nucleotide gap between the two primers. The region amplified is a 51 b.p. segment corresponding to nucleotides 83 to 133 of the published sequence of HCV-H. The primers are as follows:

```
Forward primer:
5'-CCATGGCGTTAGTATGAGTGTCGTGCAGC-3';   (SEQ ID NO:3)

Reverse primer:
5'-CCCGGGAGGGGGGGTCCTGGAG-3'.          (SEQ ID NO:4)
```

For both conventional and "nose-to-nose" PCR, the molecular beacon used for PCR product detection was 5'-FAM-ccgggcTTAGTATGAGTGTCGTGCAGC-CTgcccgg-DABCYL-3' (SEQ ID NO: 5). The stem nucleic acids are shown in lower case, and the probe loop nucleic acids (corresponding to nucleotides 91 to 113 of the HCV-H sequence) are shown in upper case.

Complementary DNA was reverse transcribed from extracted plasma RNA using either the conventional reverse primer, or the nose-to-nose reverse primer described above. Each 20 ul reaction contained 2.5 uM reverse primer, 1 unit Mo-MuLV reverse transcriptase (GIBCO BRL, Grand Island, N.Y.), 1× reverse transcriptase buffer (GIBCO BRL), 5 mM dithiothreitol (DTT), 0.06 units RNasin (Promega, Madison, Wis.), and 0.5 mM dNTPs, i.e. dATP, dTTP, dCTP and dGTP (Pharmacia, Piscataway, N.J.). Reactions were incubated at 42° C. for 45 min. The reverse transcriptase wasthen inactivated by a further incubation at 95° C. for 2 min.

For PCR amplification and detection, the products of reverse transcription were incubated in a final volume of 50 µl reaction mix containing forward primer (0.1 µM for "nose-to-nose PCR and 1 µM for conventional PCR), 1 µM reverse primer, 1.25 units AmpliTaq Gold polymerase (Applied Biosystems, Foster City, Calif.), 1× AmpliTaq Gold Buffer II (Applied Biosystems), 2 mM $MgCl_2$, 0.2 mM dNTPs, and 10 ng molecular beacon. PCR amplification was performed in the Applied Biosystems 7700 Sequence Detector using the following cycling parameters: 95° C. for 10 min (enzyme activation), followed by 44 cycles [95° C., 30 sec (denaturation); 60° C., 1 min (annealing); 72° C. (extension)]. Relative fluorescence of the molecular beacon was measured at the annealing temperature. Quantitation of HCV template molecules was achieved by inclusion of an RNA standard curve in each RT-PCR experiment. The standard curve was constructed using 10, 25, 50, $10^2$, $10^3$, $10^4$, $10^5$ or $10^6$ molecules synthetic HCV RNA Transcript diluted in 1 ug/ml yeast tRNA (Ambion, Austin, Tex.).

Table 1 shows a comparison of the three different methods for detection of eight strains of HCV. These strains are prototypes for the main HCV genotypes and subtypes. The nose-to-nose beacon assay of the present invention (A) detects all eight genotypes/subtypes, while conventional beacon PCR (B) fails to detect Genotypes 4a and 5a.

Results from the COBAS-HCM-2 assay are presented as International Units (I.U.). Although various conversion factors have been suggested (Saldanha et al, Vox Sang, 1999; 76(3):149-158; Cuijpers et al, 2001;81(1):12-20), the exact relationship between I.U. and HCV RNA copy number is still under debate, particularly for HCV genotypes other than 1a and 1b. Because of this, Roche Diagnostic Systems does not currently suggest a conversion factor for results obtained with the COBAS-HCM-2 assay. For analytical purposes, it is therefore assumed that I.U. and RNA copy number are equivalent. In comparison with the COBAS-HCM-2 assay, the nose-to-nose beacon RT-PCR assay is equivalent to or slightly more sensitive for Genotypes 1a, 1b, 2b and 6a, but is 1 log (10-fold) more sensitive for Genotype 4a, 0.5 log (3.2-fold) more sensitive for Genotypes 2a and 5a, and 0.3 log (2-fold) more sensitive for Genotype 3a. A statistical analysis comparing the relative sensitivity of the two assays is shown in Table 2.

TABLE 1

| Test Sample[1] | | A. Nose-to-Nose Beacon PCR | B. Conventional | C. COBAS HCM-2 |
|---|---|---|---|---|
| HCV Genotype/ Subtype | Virus Strain Name | ($Log_{10}$ RNA Molecules/ml) | Beacon PCR ($Log_{10}$ RNA Molecules/ml) | ($Log_{10}$ International Units/ml) |
| 1a | H strain | 5.1 | 5.0 | 4.9 |
| 1b | HC-J4/91 | 4.7 | 4.7 | 4.6 |
| 2a | HC-J6 | 5.1 | 4.2 | 4.6 |
| 2b | HC-J8 | 4.0 | 3.7 | 3.9 |

TABLE 1-continued

| Test Sample[1] | | A. Nose-to-Nose Beacon PCR | B. Conventional | C. COBAS HCM-2 |
|---|---|---|---|---|
| HCV Genotype/ Subtype | Virus Strain Name | ($Log_{10}$ RNA Molecules/ml) | Beacon PCR ($Log_{10}$ RNA Molecules/ml) | ($Log_{10}$ International Units/ml) |
| 3a | S52 | 4.3 | 3.7 | 4.0 |
| 4a | ED43 | 6.3 | <2.6 | 5.3 |
| 5a | SA13 | 5.2 | <2.6 | 4.7 |
| 6a | HK6a | 4.8 | 4.4 | 4.7 |

[1]Samples tested were plasma from chimpanzees which were infected with each of the prototype HCV strains: H strain [Inchauspe et al, Proc Natl Acad Sci (USA), 88: 10292-10296, 1991; Genbank M67463], HC-J4/91 [Okamoto et al, Virology, 190: 894-899, 1992; Genbank D10750], HC-J6 [Okamoto et al, J Gen Virol, 72: 2697-2704, 1991; Genbank D00944], HC-J8 [Okamoto et al, Virology, 188: 331-341, 1992; Genbank D10988], S52 [Bukh et al, Proc Natl Acad Sci (USA) 89: 4942-4946, 1992; Genbank M84837], ED43 [Chamberlain et al, 78: 1341-1347, 1997; Genbank Y11604], SA13 [Bukh et al, J Infect Dis, 178: 1193-1197; Genbank AF064490], HK6a [Adams et al, Bichem Biophys Res Commun, 234: 393-396, 1997; Genbank Y12083].

TABLE 2

Detection of HCV Genotypes by Nose-to-Nose Beacon PCR and COBAS HCM-2 Assays

| HCV Genotype | Nose-to-Nose Beacon PCR ($Log_{10}$ RNA Molecules/ml) x +/− s.d. (n)[1] | COBAS HCM-2 (Log 10 I.U./ml) x +/− s.d. (n) | Fold Difference[2] |
|---|---|---|---|
| 1a | 5.1 +/− 0.25 (7) | 4.9 +/− 0.12 (2) | 1.6x |
| 1b | 4.7 +/− 0.19 (7) | 4.6 +/− 0.12 (5) | 1.3x |
| 2a | 5.1 +/− 0.18 (6) | 4.6 +/− 0.22 (6) | 3.2x (p = 0.0013) |
| 2b | 4.0 +/− 0.22 (7) | 3.9 +/− 0.32 (6) | 1.3x |
| 3a | 4.3 +/− 0.11 (7) | 4.0 +/− 0.12 (6) | 2.0x (p = 0.0032) |
| 4a | 6.3 +/− 0.12 (7) | 5.3 +/− 0.33 (6) | 10x (p < 0.0001) |
| 5a | 5.2 +/− 0.12 (6) | 4.7 +/− 0.26 (6) | 3.2x (p = 0.0002) |
| 6a | 4.8 +/− 0.19 (7) | 4.7 +/− 0.90 (2) | 1.3x |

[1]Results are presented as mean +/− standard deviation of (n) replicate assays. Results from the COBAS HCM-2 assay are expressed as International Units (I.U.)

[2]Fold difference in sensitivity of the two assays is calculated as the arithmetic ratio of values obtained by Nose-to-Nose Beacon PCR to those obtained by the Roche Monitor Assay. Two-tailed P values were calculated using GraphPad InStat Software.

Screening of Plasma Samples from Individuals Infected with Diverse HCV Genotypes The "nose-to-nose" PCR of the present invention was used to screen a subset of patient plasma samples from the ICBS HCV Master Panel. This panel, which is being expanded continually, is compiled by the Centers for Disease Control (CDC) in collaboration with the International Consortium for Blood Safety (ICBS). The panel consists of plasma samples collected from diverse geographic regions. All samples are screened for HCV antibody and are subjected to genotype analysis in two independent testing laboratories at the CDC and at Visible Genetics Inc. (VGI).

A total of 192 specimens, comprising plasma samples collected in Egypt, Vietnam and Indonesia were provided by the CDC. Of these, 134 were listed as being unequivocally positive for HCV RNA on the basis of PCR-genotyping data obtained by CDC, VGI or both. Five samples were listed as having equivocal or conflicting PCR-genotype data. Fifty-three samples were listed as not genotypeable (i.e. negative for HCV RNA).

Total RNA was extracted from 70 μl freshly thawed plasma using a robotic extraction procedure in which RNA is bound and eluted from PVDF membranes in 96-well plate format (Lee and Prince, 2001, Transfusion; 41:483-487). Total RNA was obtained in a volume of 50 μl nuclease-free water. Ten microliters of this (equivalent to 14 μl plasma) were then subjected to reverse transcription and PCR using the nose-to-nose primers (SEQ ID NO: 3 and SEQ ID NO: 4) and molecular beacon (SEQ ID NO: 5) described above.

Table 2 shows the results of RT-PCR for the 134 unequivocally HCV-positive samples present in the panel. "Nose-to-nose" PCR successfully detected the vast majority of HCV isolates from all genotypes. Of the 53 samples which were not positive for HCV RNA in genotype assays, only one sample gave a weakly positive PCR signal ($10^{3.1}$ RNA molecules per ml).

Samples with a virus burden less than ~700 copies/ml (9.9 copies per 14 ul plasma) would not be detected using the combination of robotic extraction and "nose-to-nose" RT-PCR describe above. The results shown in Table 2 clearly demonstrate that the present invention permits the detection of diverse HCV genotypes with a single set of "nose-to-nose" primers and molecular beacon.

TABLE 2

| Genotype | Total Detected/Total Tested | Range ($Log_{10}$ RNA Molecules/ml Plasma) | (%) |
|---|---|---|---|
| 1a | 22/23 | 3.13-6.93 | 95.7 |
| 1b | 19/20 | 3.18-7.13 | 95.0 |
| 1c | 3/3 | 5.84-6.72 | 100 |
| 2a | 3/3 | 3.85-6.85 | 100 |
| 2e | 1/1 | 6.69 | 100 |
| 3a | 3/3 | 4.36-6.8 | 100 |
| 3b | 1/1 | 4.93 | 100 |
| 4a | 43/43 | 3.78-7.0 | 100 |
| 4d | 9/9 | 5.08-6.56 | 100 |
| 4l | 1/1 | 6.25 | 100 |
| 6a | 8/8 | 3.28-6.37 | 100 |
| 10a (3) | 5/6 | 4.22-7.23 | 83.3 |
| Ambiguous*** | 12/13 | 4.11-6.85 | 92.3 |
| TOTAL | 130/134 | | 97.0 |

***Samples for which genotyping analysis indicated mixed infection or as yet indeterminate classification have been listed separately.

Comparison of Nose-to-Nose PCR and Conventional PCR for Detection of HIV-1 Group M Subtype B Variants FIG. 6a shows an alignment of proviral DNA sequences corresponding to the V3 region and flanking sequences of four different HIV variants, all of Group M (Major) Subtype B (HIV/RT-1, HIV/RT10, HIV-38-1 and HIV/38/3). The V3 region is the most highly variable segment of the HIV genome. A molecular beacon was designed with a probe-loop structure exactly identical to variant HIV/RT-1 (nucleotides 76-97 on the V3 sequence shown). This probe sequence possesses 1, 3, or 4 mismatches with variants HIV/RT-10, HIV/38-1 and HIV/38-3 respectively (FIG. 6a).

PCR primers for "nose-to-nose" PCR were designed as follows. The forward primer (5'-acaatacaagaaaaaggataac-tatgggac-3') (SEQ ID NO: 6) corresponds to nucleotides 65-94 of the sequence of HIV/RT-1 shown in FIG. 6a. The forward primer is known as NBF. The reverse primer (5'tttctcctgttgtataaagtactctccccg-3') (SEQ ID NO: 7) corresponds to nucleotides 95-124 of the same sequence. The reverse primer is known as NBR.

Primers for conventional PCR were designed to generate a 177 b.p. PCR product as follows. The forward primer (5 'taatagtacagctgaatgaatctg-3') (SEQ ID NO: 8) corresponds to nucleotides 14-37 of the sequence of HIV/RT-1 shown in FIG. 6a. The reverse primer (5 'gttttaaagtgttattccatgc-3') (SEQ ID NO: 9) corresponds to nucleotides 168-190 of the same sequence.

FIG. 7 shows the results of an experiment to compare the ability of conventional beacon PCR with nose-to-nose PCR for detection of each of the 4 HIV variants shown in FIG. 6a. PCR reactions contained $10^6$ template molecules of HIV/RT-1, HIV/RT-10, HIV/38-1 or HIV/38-3, the molecular beacon shown in FIG. 6b, and either the conventional or nose-to-nose primers described above. Control PCR reaction contained either no template or 150 ng human genomic DNA. Amplification was performed in the Perkin Elmer 7700 using the following cycling parameters: 95° C. for 10 min, followed by 40 cycles of 95° C. for 30 sec (denaturation), 50° C. for 1 min (annealing) and 72° C. for 30 sec (extension). Fluorescence of the molecular beacon was measured at the 50° C. annealing temperature. Fluorescence was then plotted graphically against PCR cycle number. Efficiency of PCR amplification/detection is determined by the "threshold cycle" i.e. the lowest numbered PCR cycle required to generate a positive fluorescent signal.

Figure 7A:
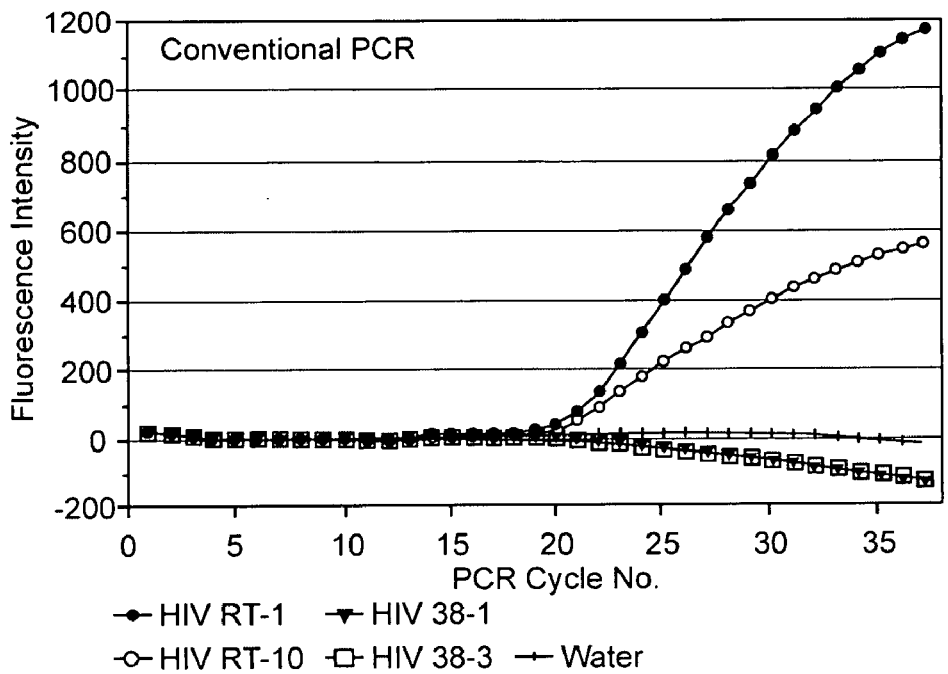
FIG. 7: Comparison of Conventional and Nose-to-Nose PCR Real Time Quantitative PCR Methods. Real Time Quantitative PCR of four different HIV variants using: (a) conventional or (b) "Nose-to-Nose" PCR methods. PCR reactions contained $10^6$ copies HIV/RT-1 (●), HIV/RT-10 (o), HIV/38-1 (▼), HIV/38-3 (□), no template (+) or 150 ng Human DNA (x).
Figure 8:
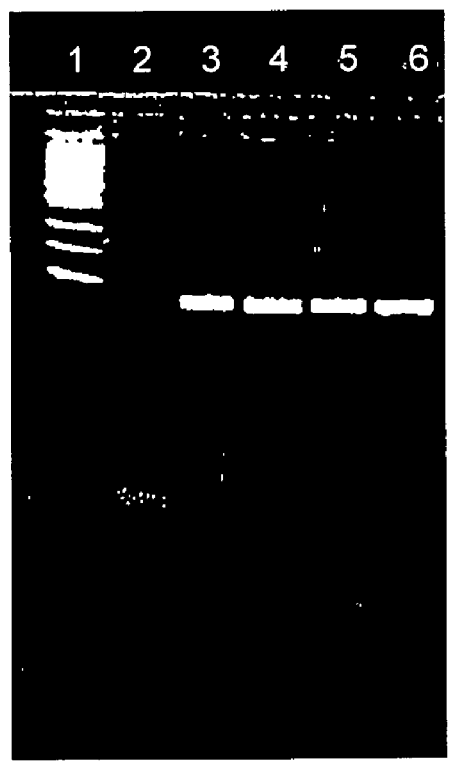
FIG. 8: Agarose Gel Analysis of Products Generated by Conventional PCR. Gel shows PCR products generated from HIV/RT-1, HIV/RT-10, HIV/38-1, and HIV/38-3 by the conventional PCR method. Lane 1: 50 bp ladder, Lane 2: No template, Lane 3: HIV/RT-1, Lane 4: HIV/RT-10, Lane 5: HIV/38-1, Lane 6: HIV/38-3.

As shown in FIG. 7a, the conventional beacon PCR technique was capable of detecting both HIV/RT-1 (exact match to the beacon) and HIV/RT-10 (one mismatch), with an equivalent threshold cycle (cycle 23) although the peak level of fluorescence obtained in the latter case was ~2 fold lower than that for the exact-match template. The conventional beacon PCR technique failed to detect either HIV/38-1 (3 mismatches) or HIV/38-3 (4 mismatches), despite the fact that PCR product was generated from all 4 variants, as shown by gel analysis (FIG. 8).

Figure 7B:
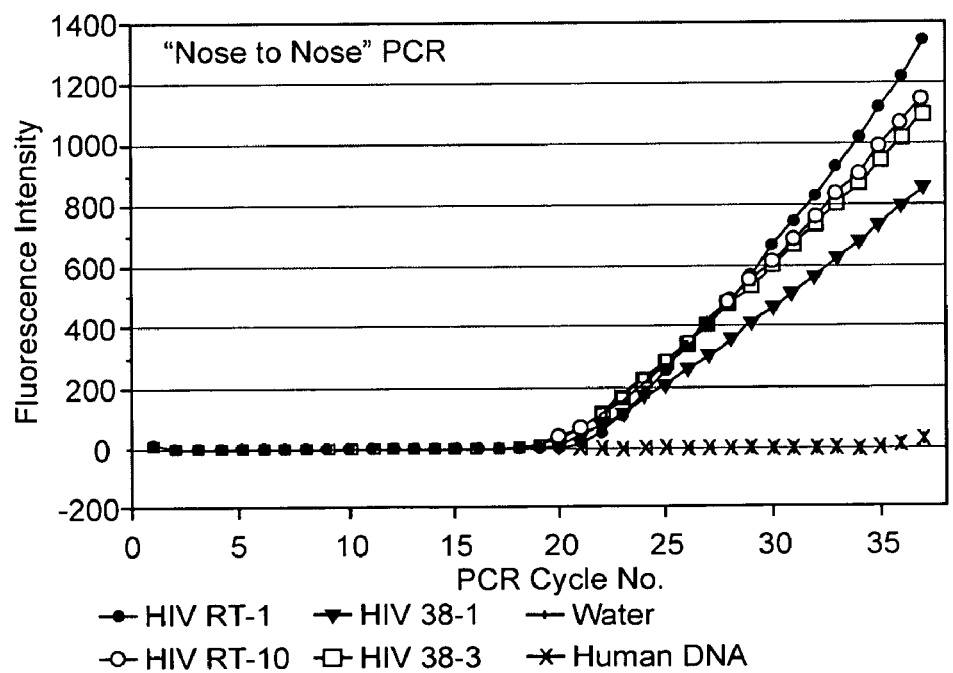

By contrast, the nose-to-nose PCR technique was capable of detecting all 4 HIV variants (0, 1, 3 or 4 mismatches) with comparable threshold cycle (FIG. 7b). Importantly, no signal was detected in reaction tubes containing either no template, or 150 ng human genomic DNA.

Detection of Different Subtypes of HIV-1 Group M

PCR primers were designed to amplify a segment of the gag gene of the HIV-1 genomic RNA, which is relatively well conserved between the different Subtypes of HIV-1 Group M. Despite this relative conservation, individual HIV-1 Subtypes show up 20% nucleotide sequence diversity within this region of the genome (Roberton et al, 1999 in: Human Retroviruses and AIDS 1999, pp 492-505, Editors Kuiken et al, Los Alamos National Laboratory, Los Alamos, N. Mex.).

Conventional primers for beacon PCR were designed to amplify a 94 b.p. segment of RNA corresponding to nucleotides 1478 to 1571 of the published sequence of the Subtype B HIV-1 isolate HXB2 [Ratner et al, 1985, Nature, 313(6000):277-284; Genbank K03455]. The intervening gap between the two conventional RT-PCR primers is 53 b.p. The primers are as follows:

Forward primer: 5'-AACCAAGGGGAAGTGACATA-3' (SEQ ID NO: 10);
Reverse primer: 5'-ATTTCTCCTACTGGGATAGGT-3' (SEQ ID NO: 11).

The primers for "nose-to-nose" RT-PCR of the present invention were designed to amply a 57 b.p. segment corresponding to nucleotides 1502 to 1558 of the published sequence of HIV-1 HXB2. There is no intervening gap between the two primers. The primers are as follows Forward primer: 5'-GAACTACTAGTACCCTTCAGGAACAAATAG-3'; (SEQ ID NO:12)

Reverse primer: 5'-GGATAGGTGGATTATTTGTCATCCATC-3'. (SEQ ID NO:13)

For both conventional and "nose-to-nose" PCR, the molecular beacon used for PCR product detection was 5'-FAM-cgcctTACCCTTCAGGAACAAATAGaggcg-DABCYL-3' (SEQ ID NO: 14). The stem nucleic acids are shown in lower case, and the probe loop nucleic acids (corresponding to nucleotides 1512 to 1530 of the HIV-1 HXB2 sequence) are shown in upper case.

Virus isolates from HIV-1 Subtypes A, B, C, D, F and G were obtained as cell-free culture supernatants from the AIDS Research and Reference Reagent Program, Division of AIDS, NIAID, NIH. RNA was extracted from 140 ul freshly thawed culture supernatant Complementary DNA was reverse transcribed from extracted RNA using either the conventional reverse primer, or the nose-to-nose reverse primer described above. Reaction conditions for both cDNA synthesis and PCR amplification were essentially the same as those described above for HCV. All assays were carried out in triplicate. Quantitation of HIV template molecules was achieved by inclusion of an RNA standard curve in each RT-PCR experiment. The standard curve was constructed using 1, 10, $10^2$, $10^3$, $10^4$, $10^5$ or $10^6$ molecules HIV-1 RNA diluted in 1 µg/ml yeast tRNA (Ambion, Austin, Tex.).

Table 3 shows a comparison of conventional RT-PCR and "nose-to-nose" RT-PCR for detection of HIV-1 Subtypes. The "nose-to-nose" assay of the present invention (A.) detects all 6 HIV-1 Subtypes tested, while the conventional assay fails to detect Subtypes A, D and G.

TABLE 3

| | | Log$_{10}$ RNA molecules per ml of culture supernatant detected by: | |
|---|---|---|---|
| Test Sample[1] | | Conventional | "Nose-to-Nose" |
| HIV-1 Subtype | Virus Strain Name | Beacon RT-PCR | Beacon RT-PCR |
| A | 92UG029[2] | <3.9 | 9.7 +/− 0.05 |
| B | 92BR014[2] | 9.3 +/− 0.3 | 9.3 +/− 0.1 |
| C | 92BR025[2] | 9.4 +/− 0.2 | 9.2 +/− 0.3 |
| D | 94UG114[2] | <3.9 | 10.2 +/− 0.06 |
| F | 93BR020[2] | 4.8 +/− 0.6 | 5.6 +/− 0.2 |
| G | Jv1083[3] | <3.9 | 9.8 +/− 0.2 |
| No Template | — | <3.9 | <3.9 |

[1]Test samples were virus isolates obtained as cell-free culture supernatants from the AIDS Research and Reference Reagent Program, Division of AIDS, NIAID,NIH.
[2]Isolates contributed by The UNAIDS Network for HIV Isolation and Characterization, and the DAIDS, NIAID.
[3]Abimiku et al, 1994, AIDS Res Hum Retroviruses, 10(11): 1581-1583.

Adaptation of the Method for Simultaneous Detection of Both HIV-1 Group M and HIV-1 Group O Variants Virus isolates from HIV-1 Group 0 (Outlier) show marked sequence variation from members of HIV-1 Group M (Major). Although Group O viruses are mainly prevalent in parts of Africa, their frequency among samples collected by blood banks outside Africa appears to be increasing (Jaffe and Schochetman, 1998, Infect Dis Clin North Am; 12(1):3946; Couturier et al, 2000, AIDS; 14(3):289-296; Fed Regist, Sep. 23, 1997;62(184):49695). The present invention permits detection of members of both Group M and Group O using a single set of "nose-to-nose" primers and molecular beacon.

The primers for "nose-to-nose" RT-PCR of the present invention were designed to amplify a 64 b.p. segment of the pol gene of the HIV-1 genomic RNA, corresponding to nucleotides 4750 to 4813 of the published sequence of HIV-1 HXB2. There is no intervening gap between the two primers. The primers are as follows

```
Forward primer:  5'-CAGCAGTACAAATGGCAGTATTCATTCACAATTT-3'; (SEQ ID NO:15)

Reverse primer:  5'-CTGTATCCCCCAATCCCCCCTTTTCTTTTTA-3'.  (SEQ ID NO:16)
```

The molecular beacon used for PCR product detection was 5'-FAM-cgcacgGCAGTATTCATTCAC-CAATTTTcgtgcg-DABCYL-3' (SEQ ID NO: 17). The stem nucleic acids are shown in lower case, and the probe loop nucleic acids are shown in upper case.

The new primers and beacon were then tested for their ability to amplify and detect virus isolates from HIV-1 Group M (Subtypes A, B, C, D, F and G) and Group 0, which were obtained as cell-free culture supernatants from the AIDS Research and Reference Reagent Program, Division of AIDS, NIAID/NIH. Prior to RNA extraction, all cell supernatants were diluted 1000-fold in phosphate buffered saline (PBS). RNA extraction was performed on the diluted supernatant essentially as described above, except that following isolation, all RNA samples were treated with RNase-free DNase (Ambion, Austin, Tex.) to ensure removal of contaminating proviral DNA. Complementary DNA was reverse transcribed from extracted RNA using the nose-to-nose reverse primer (SEQ ID NO: 16) described above. Reaction conditions for both cDNA synthesis and PCR amplification were essentially the same as those described above. Quantitation of HIV-1 template molecules was achieved by inclusion of an RNA standard curve in each RT-PCR experiment.

Table 4 shows the results of RT-PCR using the pol region "nose-to-nose" primers of the present invention, and a comparison with the COBAS AMPLICOR HIV-1 Monitor Assay Version 1.0 (Roche Diagnostics, Branchburg, N.J.). The "nose-to-nose" RT-PCR assay was capable of detecting all Group M and Group O isolates tested, with sensitivity equal to (Group M, Subtypes B and C) or greater than (Group M, Subtypes A, D and F) the COBAS AMPLICOR HIV-1 Monitor Assay (1.0). The latter assay failed to detect either of the Group O virus isolates tested, and also failed to detect Group M Subtype G. These data are in agreement with a recent report that neither the COBAS AMPLICOR HIV-1 Monitor Assay (1.0) nor its improved version (1.5) are capable of detecting group 0 viruses (Yang et al, Transfusion, 2001;41:643-651). In contrast, the present invention permits detection of all virus isolates with a single set of "nose-to-nose" primers and molecular beacon.

TABLE 4

| Test Sample[1] | | Log$_{10}$ RNA molecules per ml of diluted culture Supernatant detected by: | |
|---|---|---|---|
| HIV-1 Subtype | Virus Strain[2] Name | "Nose-to-Nose" Beacon RT-PCR | COBAS Amplicor HIV-1 Monitor Version 1.0 |
| A | 92UG029 | 5.1 +/− 0.17 | 3.5 +/− 0.10 |
| B | 92BR014 | 5.4 +/− 0.62 | 5.2 +/− 0.03 |
| C | 92BR025 | 5.6 +/− 0.04 | 5.5 +/− 0.04 |
| D | 94UG114 | 5.9 +/− 0.46 | 5.2 +/− 0.05 |
| F | 93BR020 | 5.7 +/− 0.80 | 3.7 +/− 0.09 |
| G | Jv1083 | 7.3 +/− 0.08 | Negative |
| O | L20571 | 5.4 +/− 0.66 | Negative |
| O | Y14496 | 6.0 +/− 0.38 | Negative |
| Human DNA (100 ng)[3] | | <3.0 | Not Tested |
| Human RNA (100 ng)[3] | | <3.0 | Not Tested |

[1]Prior to RNA extraction, all cell free supernatants were diluted 1000 fold in either PBS (for "nose-to-nose" RT-PCR) or normal human plasma (for COBAS Amplicor HIV-1 Monitor Version 1.0).
[2]Virus isolates are as described in Table 3; isolate L20571, Gurtler LG et al, 1994, J Virol, 68: 1581; isolate Y14496, Loussert-Ajaka I, et al. J Virol 69: 5640, 1995.
[3]"Nose-to-Nose" PCR or RT-PCR was also performed on 100 ng of human DNA or RNA to verify that the observed signals were due to virus amplification, and not amplification of contaminating human nucleic acids.

We claim:

1. In a primer extension chain reaction method for determining the presence of a target nucleic acid molecule in a sample, the method comprising:
   (a) hybridizing a reverse primer to the target nucleic acid molecule under conditions suitable for carrying out a primer extension chain reaction;
   (b) extending the reverse primer using the target nucleic acid molecule as a template to form a reverse primer extension product, wherein the reverse primer joined to the reverse primer extension product constitutes a reverse primer amplification product;
   (c) denaturing the reverse primer amplification product from its template;
   (d) hybridizing a forward primer to:
      (i) a nucleic acid molecule which is complementary to the target nucleic acid molecule, if present; or
      (ii) the reverse primer amplification product;
   (e) extending the forward primer using the complementary target nucleic acid molecule, if present, or the reverse primer amplification product, as a template, wherein the forward primer joined to the forward primer extension product constitutes a forward primer amplification product;
   (f) denaturing the forward primer amplification product from its template;
   (g) hybridizing the reverse primer to the forward primer amplification product;
   (h) extending the reverse primer using the forward primer amplification product as a template to form an additional reverse primer extension product, wherein the reverse primer joined to the additional reverse primer extension product constitutes an additional reverse primer amplification product;
   (i) denaturing the additional reverse primer amplification product from its template;
   (j) hybridizing the forward primer to the reverse primer amplification product;
   (k) extending the forward primer using the reverse primer amplification product as a template to form an additional forward primer extension product, wherein the forward primer joined to the additional forward primer extension product constitutes an additional forward primer amplification product;
   (l) denaturing the additional forward primer amplification product from its template;
   (m) repeating steps (g) through (l), using the additional reverse primer amplification product and the additional forward primer amplification product as templates for the forward primer and the reverse primer, respectively, a sufficient number of times to produce a detectable quantity of additional reverse primer amplification product or of additional forward primer amplification product; and
   (n) detecting the presence of the additional reverse primer amplification product or the additional forward primer amplification product;

the improvement wherein the nucleotide at the 3' end of the reverse primer hybridizes with:

(i) the nucleotide at the 5' end of the forward primer extension product or of the additional forward primer extension product; or
(ii) a nucleotide separated from the nucleotide at the 5' end of the forward primer extension product or of the additional forward primer extension product by a gap of nucleotides, wherein the gap comprises a sequence known to be highly conserved; and wherein the nucleotide at the 3' end of the forward primer hybridizes with:
(i) the nucleotide at the 5' end of the reverse primer extension product or of the additional reverse primer extension product; or
(ii) a nucleotide separated from the nucleotide at the 5' end of the reverse primer extension product or of the additional reverse primer extension product by a gap of nucleotides, wherein the gap comprises a sequence known to be highly conserved.

2. The method according to claim 1 wherein the target nucleic acid molecules are known to have variant sequences.

3. The method according to claim 1 wherein the primer extension chain reaction is a polymerase chain reaction (PCR).

4. The method according to claim 1 wherein the target nucleic acid molecule is a virus.

5. The method according to claim 4 wherein the virus is human immunodeficiency virus (HIV).

6. The method according to claim 4 wherein the virus is hepatitis C virus (HCV) or hepatitis B virus (HBV).

7. The method according to claim 4 wherein the gap comprises a highly conserved region of the genome of the virus.

8. The method according to claim 1 wherein the gap comprises from about one to about five nucleotides.

9. The method according to claim 8 wherein the gap comprises about two nucleotides.

10. The method according to claim 3 wherein the nucleic acid molecule which is complementary to the target nucleic acid molecule of step (d)(i) is provided separately as the cDNA of the target nucleic acid molecule.

11. The method according to claim 1 wherein detecting the presence of the additional reverse primer amplification product or the additional forward primer amplification product comprises:
(A) providing a self-altering signal-generating probe, wherein the probe comprises:
(i) a first nucleic acid sequence attached to a reporter moiety capable of generating a detectable signal;
(ii) a second nucleic acid sequence that:
(a) is complementary to the first nucleic acid sequence, and
(b) is attached to an interactive moiety capable of altering the signal of the reporter moiety when the first nucleic acid sequence and the second nucleic acid sequence are hybridized to each other; and
(iii) a probe sequence which connects the first nucleic acid sequence and the second nucleic acid sequence; wherein the probe sequence comprises either:
(a) the nucleotide sequence of a segment of the forward primer; or
(b) the nucleotide sequence of a segment of the reverse primer; and
(B) contacting the amplification products with the probe;
wherein when the probe sequence of the probe hybridizes with the additional reverse primer amplification product or with the additional forward primer amplification product, the first and second nucleic acid sequences become denatured, thereby generating a signal by the reporter moiety; and
wherein the signal generated by the reporter moiety indicates the presence of the target molecule.

12. The method according to claim 11 wherein the probe sequence comprises either:
(a) the nucleotide sequence of a segment of the forward primer, and not the nucleotide sequence of a segment which is complementary to the reverse primer; or
(b) the nucleotide sequence of a segment of the reverse primer, and not the nucleotide sequence of a segment which is complementary to the forward primer.

13. The method according to claim 11 wherein the probe sequence comprises either:
(a) the nucleotide sequence of a segment of the forward primer and the nucleotide sequence of a segment which is complementary to the reverse primer; or
(b) the nucleotide sequence of a segment of the reverse primer and the nucleotide sequence of a segment which is complementary to the forward primer.

14. The method according to claim 11 wherein the level of the detectable signal generated by the probe is proportional to the quantity of the target nucleic acid molecule in the sample.

15. The method according to claim 13 wherein about sixty to about ninety-five percent of the probe sequence comprises either:
(i) the nucleotide sequence of a segment of the forward primer; or
(ii) the nucleotide sequence of a segment of the reverse primer.

16. The method according to claim 11 wherein:
if the probe sequence comprises the nucleotide sequence of a segment of the reverse primer, the molar ratio of the reverse primer to the forward primer is in the range from about 1:5 to about 1:20; or
if the probe sequence comprises the nucleotide sequence of a segment of the forward primer, the molar ratio of the forward primer to the reverse primer is in the range from about 1:5 to about 1:20.

17. The method according to claim 11 wherein the probe sequence comprises from about ten to about thirty nucleotide residues.

18. The method according to claim 17 wherein the probe sequence comprises from about eighteen to about twenty-four nucleotide residues.

19. The method according to claim 11 wherein the detectable signal is a luminescent signal.

20. The method according to claim 19 wherein the luminescent signal is a fluorescent signal.

21. The method according to claim 19 wherein the luminescent signal is chemiluminescent signal.

22. The method of claim 11 wherein the reporter moiety is attached at the 5' terminus or 3' terminus of the self-altering signal-generating probe.

23. The method of claim 11 wherein the interactive moiety is attached at the 5' terminus or 3' terminus of the self-altering signal-generating probe.

24. The method according to claim 11 wherein the reporter moiety is a fluorophore.

25. The method according to claim 24 wherein the fluorophore is a xanthene dye, a cyanine dye, a dansyl derivative, EDANS, coumarin, Lucifer yellow, BODIPY, Cy3, Cy5, Cy7, Texas red, erythrosine, naphthylamine, Oregon green, or combinations thereof.

26. The method according to claim 25 wherein the xanthene dye is a fluorescein or a rhodamine.

27. The method according to claim 26 wherein the fluorescein is selected from the group consisting of 5-carboxyfluorescein (5-FAM); 6-carboxyfluorescein (6-FAM); 2',4',1,4,-tetrachlorofluorescein (TET); 2',4',5',7',1,4-hexachlorofluorescein (HEX); eosin; calcium green; and NED.

28. The method according to claim 26 wherein the rhodamine is selected from the group consisting of tetramethyl-6-carboxyrhodamine (TAMRA); tetrapropano-6-carboxyrhodamine (ROX); 2',7' dimethoxy-4',5-dichloro-6-carboxyrhodamine (JOE); and tetramethylrhodamine.

29. The method according to claim 11 wherein the interactive moiety is a quencher.

30. The method according to claim 29 wherein the quencher is DABCYL, anthroquinone, nitrothiazole, nitroimidazole or malachite green.

31. The method according to claim 30 wherein the DABCYL is DABSYL, DABMI or methyl red.

32. The method according to claim 11 wherein the interactive moiety is a fluorophore.

33. The method of claim 1 wherein the amplification products are measured and quantitated by end-point analysis.

34. The method of claim 1 wherein the amplification products are measured and quantitated by real-time analysis.

35. The method of claim 1 wherein the amplification products are measured using a standard curve derived from a series of threshold cycle measurements.

* * * * *